United States Patent
Tan et al.

(10) Patent No.: US 10,354,377 B2
(45) Date of Patent: Jul. 16, 2019

(54) TECHNIQUES FOR SEGMENTATION OF LYMPH NODES, LUNG LESIONS AND OTHER SOLID OR PART-SOLID OBJECTS

(71) Applicants: Yongqiang Tan, Forest Hills, NY (US); Binsheng Zhao, Forest Hills, NY (US); Lawrence H. Schwartz, New York, NY (US)

(72) Inventors: Yongqiang Tan, Forest Hills, NY (US); Binsheng Zhao, Forest Hills, NY (US); Lawrence H. Schwartz, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 624 days.

(21) Appl. No.: 14/394,098

(22) PCT Filed: Apr. 11, 2013

(86) PCT No.: PCT/US2013/036258
§ 371 (c)(1),
(2) Date: Oct. 12, 2014

(87) PCT Pub. No.: WO2013/155358
PCT Pub. Date: Oct. 17, 2013

(65) Prior Publication Data
US 2015/0078641 A1    Mar. 19, 2015

Related U.S. Application Data

(60) Provisional application No. 61/622,989, filed on Apr. 11, 2012, provisional application No. 61/622,998, filed on Apr. 11, 2012.

(51) Int. Cl.
G06T 15/06    (2011.01)
G06T 7/12    (2017.01)
(Continued)

(52) U.S. Cl.
CPC ............. *G06T 7/0012* (2013.01); *G06T 7/12* (2017.01); *G06T 7/136* (2017.01); *G06T 7/149* (2017.01);
(Continued)

(58) Field of Classification Search
CPC ... G06T 7/0012; G06T 7/0081; G06T 7/0083; G06T 7/11; G06T 2207/10081;
(Continued)

(56) References Cited

U.S. PATENT DOCUMENTS 5,551,431 A * 9/1996 Wells, III ........... G01R 33/5659
324/307
6,259,802 B1 * 7/2001 Jolly ....................... G06T 7/246
382/103

(Continued)

OTHER PUBLICATIONS

Elter et al., Contour tracing for segmentation of mammographic masses, Aug. 24, 2010 [retrieved Aug. 9, 2016], Physics in Medicine and Biology, vol. 55, No. 18, pp. 5299-5315. Retrieved from the Internet: http://iopscience.iop.org/article/10.1088/0031-9155/55/18/004/meta.*

(Continued)

*Primary Examiner* — Andrew M Moyer
*Assistant Examiner* — Dennis Rosario
(74) *Attorney, Agent, or Firm* — Beusse Wolter Sanks & Maire PLLC; Eugene Molinelli

(57) ABSTRACT

Techniques for segmentation include determining an edge of voxels in a range associated with a target object. A center voxel is determined. Target size is determined based on the center voxel. In some embodiments, edges near the center are suppressed, markers are determined based on the center, and an initial boundary is determined using a watershed transform. Some embodiments include determining multiple rays originating at the center in 3D, and determining adjacent rays for each. In some embodiments, a 2D field of (Continued)

amplitudes is determined on a first dimension for distance along a ray and a second dimension for successive rays in order. An initial boundary is determined based on a path of minimum cost to connect each ray. In some embodiments, active contouring is performed using a novel term to refine the initial boundary. In some embodiments, boundaries of part-solid target objects are refined using Markov models.

19 Claims, 17 Drawing Sheets

(51) Int. Cl.
  G06T 7/00 (2017.01)
  G06T 7/149 (2017.01)
  G06T 7/155 (2017.01)
  G06T 7/136 (2017.01)
(52) U.S. Cl.
  CPC .............. *G06T 7/155* (2017.01); *G06T 15/06* (2013.01); *G06T 2207/10072* (2013.01); *G06T 2207/10081* (2013.01); *G06T 2207/20116* (2013.01); *G06T 2207/20152* (2013.01); *G06T 2207/20168* (2013.01); *G06T 2207/30061* (2013.01); *G06T 2207/30064* (2013.01); *G06T 2207/30096* (2013.01)
(58) Field of Classification Search
  CPC ........... G06T 2207/20152; G06T 7/155; G06T 2207/30024; G06T 7/12; G06T 2207/10056; G06T 2207/30101; G06T 2210/41; G06T 2207/30061; G06T 2207/10072; G06T 2207/30096; G06T 15/08; G06T 15/06; G06K 9/0014; G06K 9/342; G06K 7/13; G06K 2207/20192; G06K 9/4671; A61B 5/4528
  See application file for complete search history.

(56) References Cited

U.S. PATENT DOCUMENTS

| | | | | |
|---|---|---|---|---|
| 6,694,163 B1* | 2/2004 | Vining | ................. | G06T 17/00 128/920 |
| 7,454,045 B2* | 11/2008 | Yao | ................... | G06K 9/00201 382/128 |
| 8,150,120 B2* | 4/2012 | Gindele | ............... | G06T 7/0081 345/424 |
| 8,435,181 B2* | 5/2013 | Yang | ................... | A61B 8/0858 600/437 |
| 8,884,618 B2* | 11/2014 | Mahfouz | .............. | A61F 2/3094 324/309 |
| 2002/0006216 A1* | 1/2002 | Armato, III | ......... | G06T 7/0012 382/131 |
| 2008/0317314 A1* | 12/2008 | Schwartz | ................ | G06K 9/34 382/131 |
| 2010/0183225 A1 | 7/2010 | Vantaram et al. | | |
| 2011/0026798 A1 | 2/2011 | Madabhushi et al. | | |

OTHER PUBLICATIONS

Nguyen et al, Watersnakes: Energy-Driven Watershed Segmentation, Mar. 2003 [retrieved Aug. 9, 2016], IEEE Transactions on Pattern Analysis and Machine Intelligence, vol. 25, Issue: 3, pp. 330-342. Retrieved from the Internet: http://ieeexplore.ieee.org/xpls/abs_all.jsp?arnumber=1182096&tag=1.*

Yezzi et al, A Geometric Snake Model for Segmentation of Medical Imagery, Apr. 1997 [retrieved Aug. 9, 2016], IEEE Transactions on Medical Imaging, vol. 16, Issue: 2, pp. 199-209. Retrieved from the Internet: http://ieeexplore.ieee.org/xpls/abs_all.jsp?arnumber=563665 &tag=1.*

Strickland et al., Development of Subject-Specific Geometric Spine Model through Use of Automated Active Contour Segmentation and Kinematic Constraint-Limited Registration, Oct. 2011 [retrieved Jan. 11, 2018], Journal of Digital Imaging, vol. 24, Issue 5, pp. 926-942. Retrieved Internet: https://rd.springer.com/article/10.1007/s10278-010-9336-z.*

Thurey et al., A Multiscale Approach to Mesh-based Surface Tension Flows, Jul. 2010 [retrieved Jan. 15, 2018], ACM Transactions on Graphics (TOG)—Proceedings of ACM SIGGRAPH 2010, vol. 29, Issue 4, Article No. 48,pp. 48:1-48:10. Retrieved from the Internet: https://dl.acm.org/citation.cfm?id=1778785.*

Zhang et al., Active Contours driven by local image fitting energy, Apr. 2010 [retrieved Jan. 15, 2018], Pattern Recognition, vol. 43, Issue 4, pp. 1199-1206. Retrieved from the Internet: http://www.sciencedirect.com/science/article/pii/S0031320309003835.*

Esedoglu et al., A Variational Formulation for a Level Set Representation of Multiphase Flow and Area Preserving Curvature Flow, 2008 [retrieved Jan. 15, 2018], Communications in Mathematical Science, vol. 6, No. 1,pp. 125-148. Retrieved from the Internet: https://projecteuclid.org/euclid.cms/1204905780.*

Geets et al., A Gradient-based method for segmenting FDG-PET images:methodology and validation, Sep. 2007 [retrieved Jan. 15, 2018], European Journal of Nuclear Medicine and Molecular Imaging, vol. 34, Issue 34,pp. 1427-1438. Retrieved from the Internet: https://rd.springer.com/article/10.1007/s00259-006-0363-4.*

Delingette et al., Shape and Topology Constraints on Parametric Active Contours, Aug. 2001 [retrieved Jan. 15, 2018], Computer Vision and Image Understanding, vol. 83, Issue 2, pp. 140-171. Retrieved from the Internet: http://www.sciencedirect.com/science/article/pii/S1077314201909208.*

Yang et al., Automatic centerline extraction of coronary arteries in coronary computed tomographic angiography, Jun. 3, 2011 (first on-line)[retrieved Sep. 15, 2018], The International Journal of Cardiovascular Imaging, vol. 28, Issue:4,pp. 921-933. Retrieved from the Internet: https://link.springer.com/article/10.1007/s10554-011-9894-2.*

Gibou, Frederic, and Ronald Fedkiw, "A Fast Hybrid k-Means Level Set Algorithm for Segmentation", 2002, pp. 1-11, Publisher: 4th Annual Hawaii International Conference on Statistics and Mathematics, 2002, Published in: physbam.stanford.edu/~fedkiw/papers/stanford2002-08.pdf.

ISA/US, "International Search Report and Written Opinion for the corresponding PCT application No. 2013/036258", dated Aug. 6, 2013, pp. 1-11 .

Lu, Xiaoye, and Roberto Manduchi, "Fast image motion segmentation for surveillance applications", "Image and Vision Computing", 2011, pp. 104-116, vol. 29, Publisher: Elsevier, Published in: http://users.soe.ucsc.edu/~manduchi/papers/sdarticle.pdf.

Armato, Samuel G., et al., "Method, System and Computer Readable Medium for the Two-Dimensional and Three-Dimensional Detection of Lesions in Computed Tomography Scans", Jan. 17, 2002.

Zhu, Yanjie, et al., "Automatic Segmentation of Ground-Glass Opacities in Lung CT Images by Using Markov Random Field-Based Algorithms", "J Digit Imaging", 2011, pp. 409-422, vol. 25, Publisher: Society for Imaging Informatics in Medicine, Published in: http://www.ncbi.nlm.nih.gov/pmc/articles/PMC3348983/pdf/10278_2011_Article_9435.pdf.

* cited by examiner

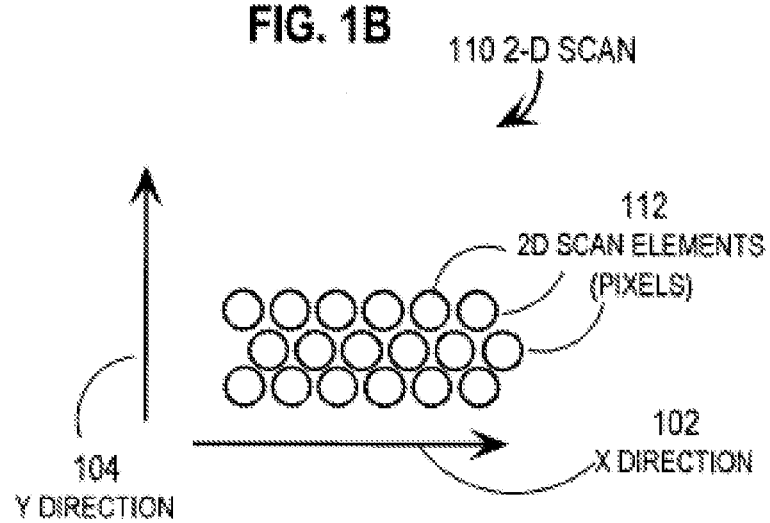
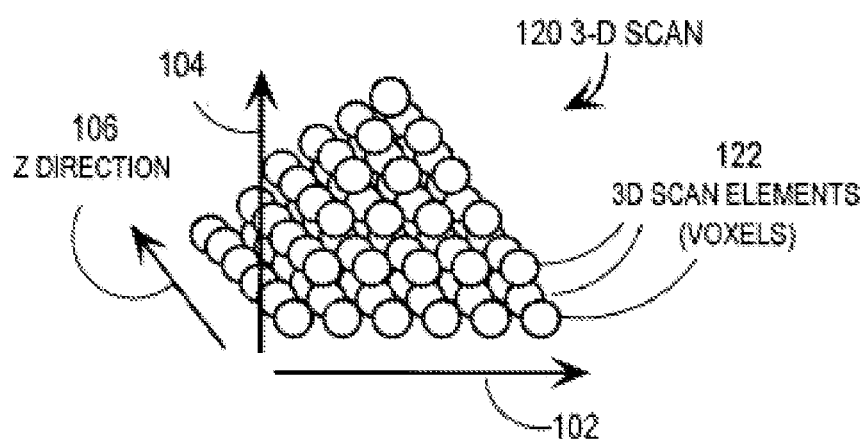

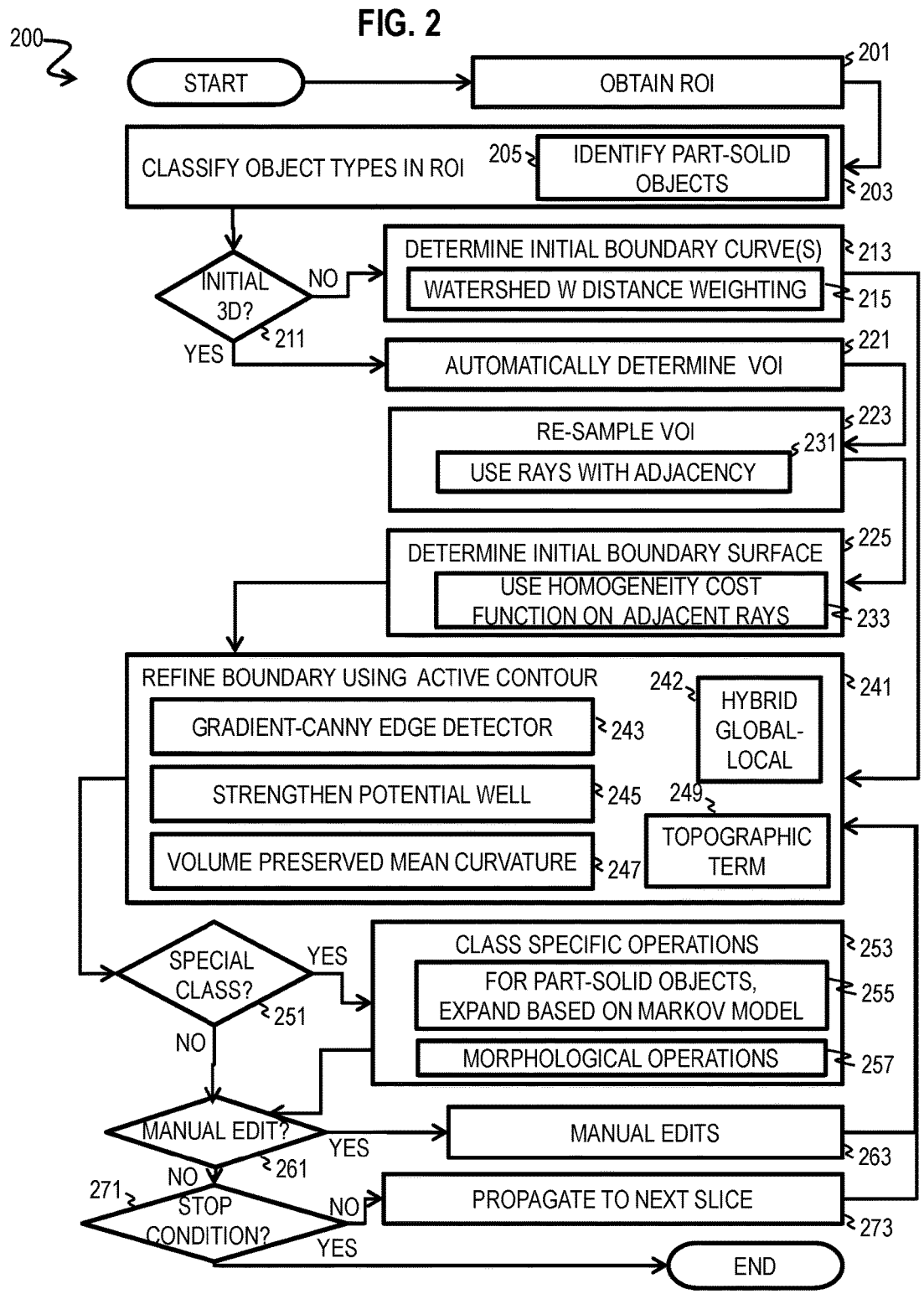

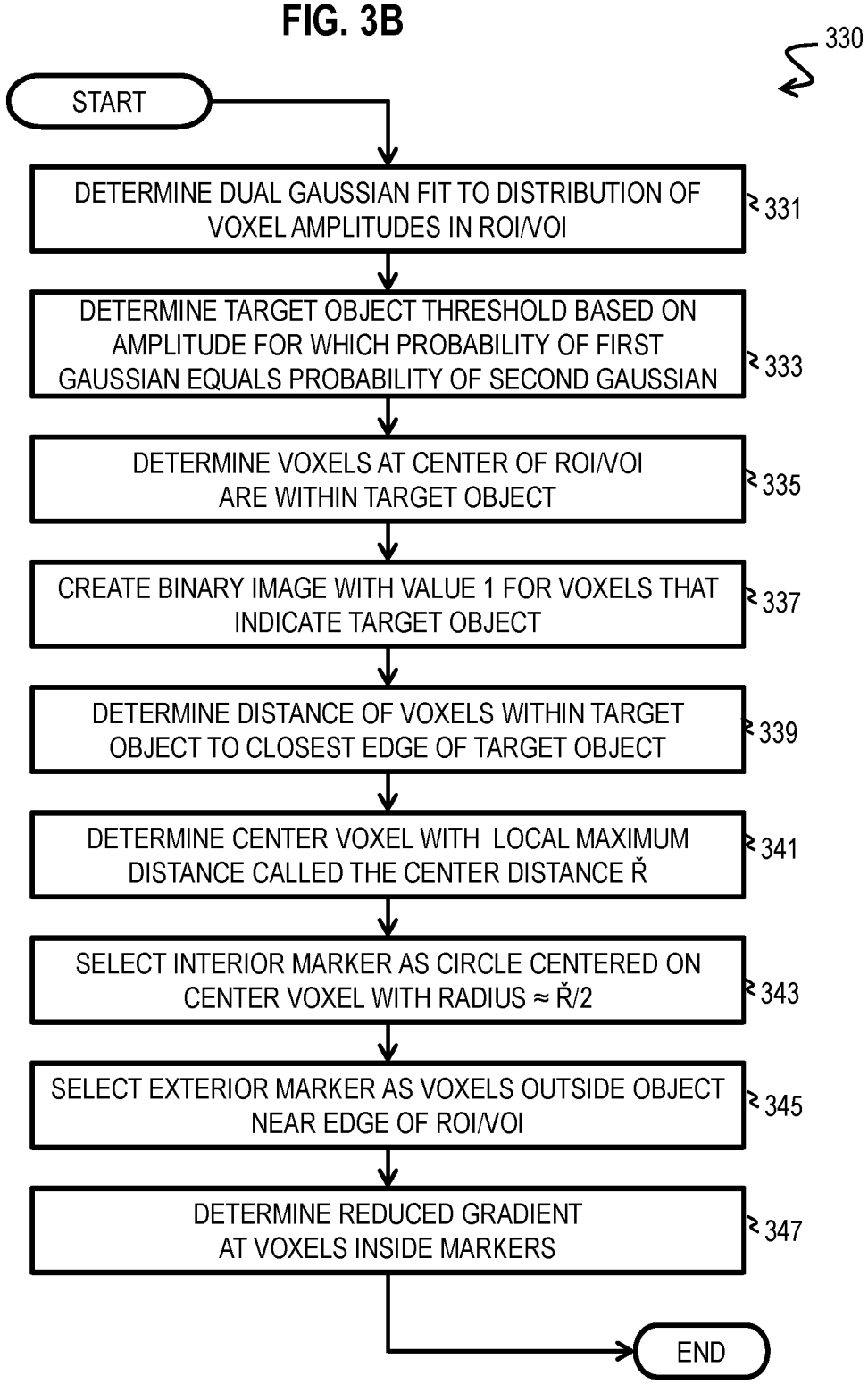

VERTICES 711

RAYS 721

VERTICES 712

RAYS 722

VERTICES 713

RAYS 723

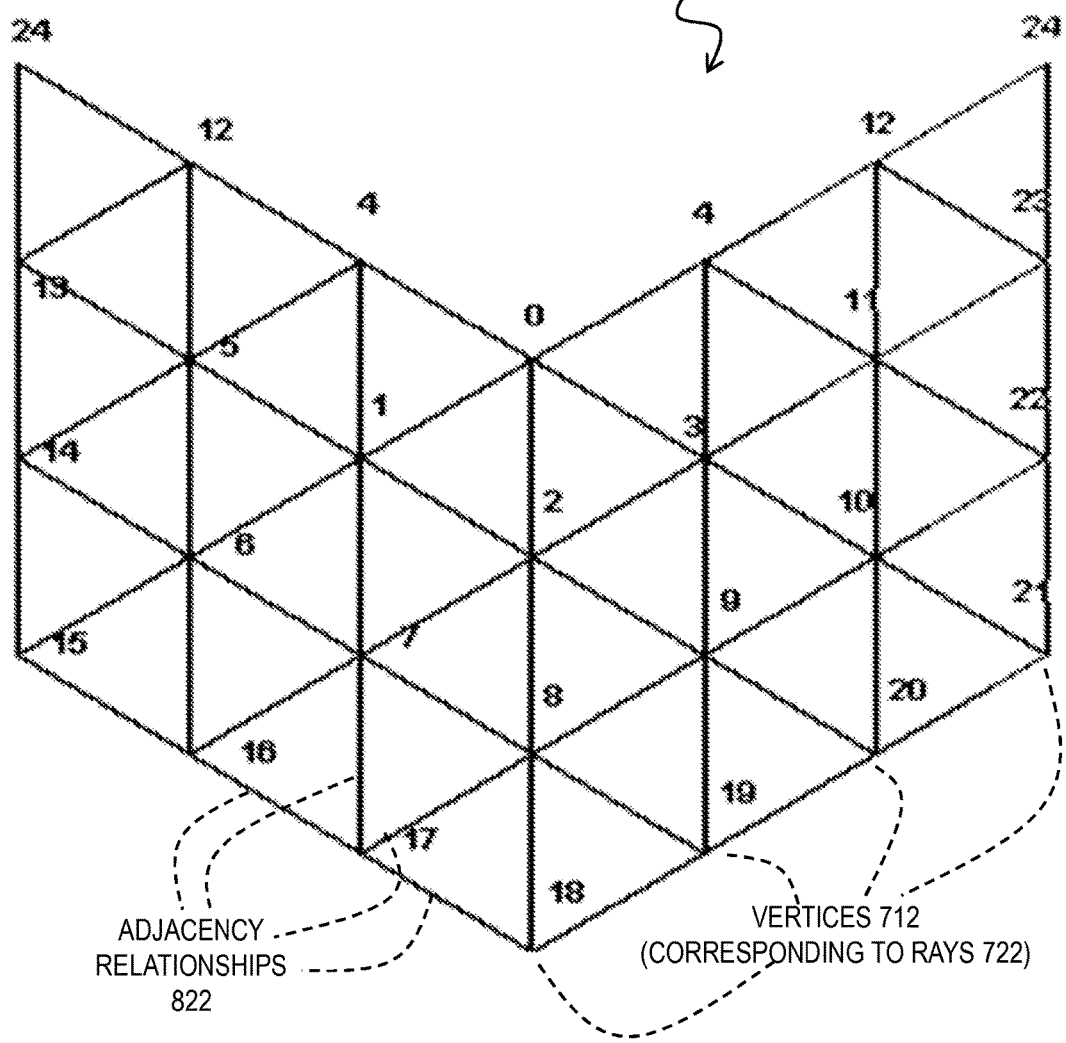

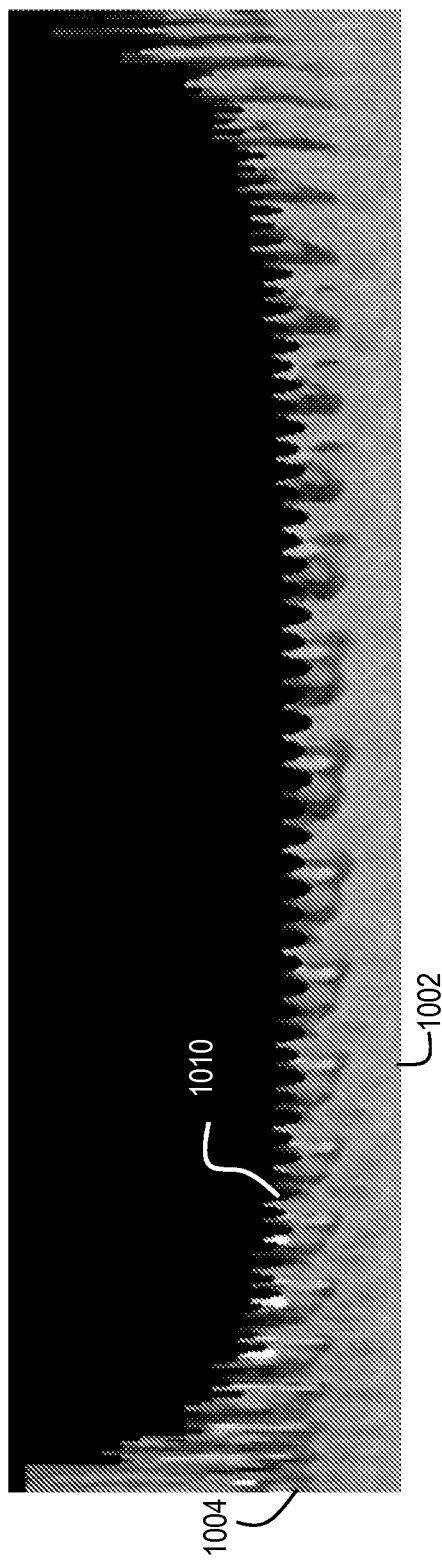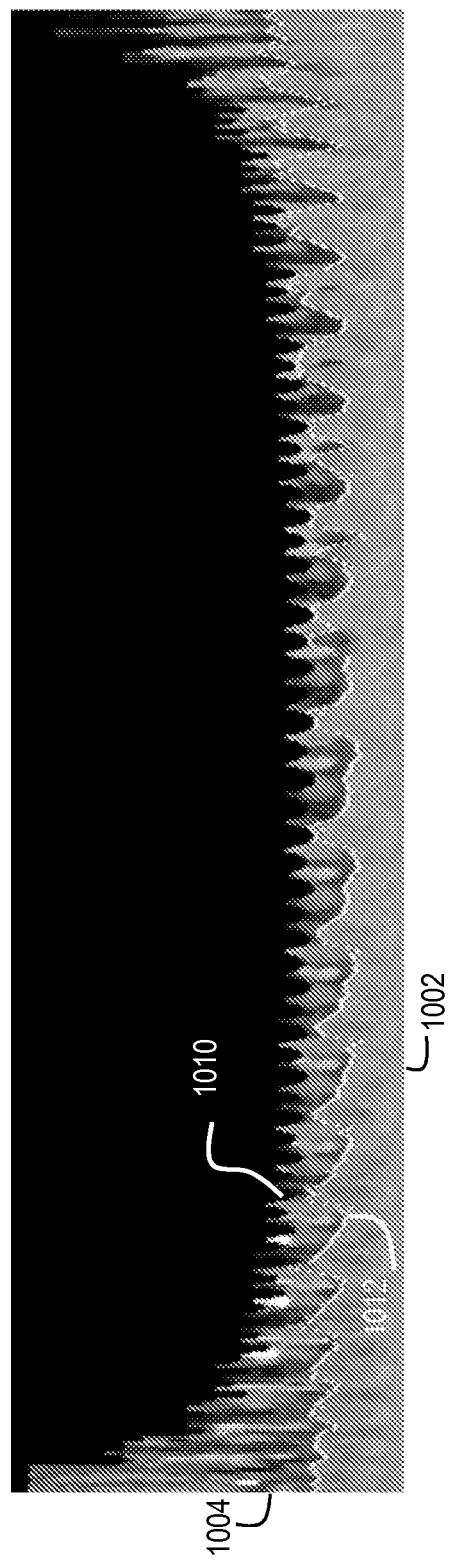

TECHNIQUES FOR SEGMENTATION OF LYMPH NODES, LUNG LESIONS AND OTHER SOLID OR PART-SOLID OBJECTS

CROSS-REFERENCE TO RELATED APPLICATIONS

This application claims benefit of Provisional Appln. 61/622,989, filed Apr. 11, 2012, the entire contents of which are hereby incorporated by reference as if fully set forth herein, under 35 U.S.C. § 119(e).

This application claims benefit of Provisional Appln. 61/622,998, filed Apr. 11, 2012, the entire contents of which are hereby incorporated by reference as if fully set forth herein, under 35 U.S.C. § 119(e).

STATEMENT OF GOVERNMENTAL INTEREST

This invention was made with government support under Contract No. CA149490 and CA140207 awarded by the National Institutes of Health. The government has certain rights in the invention.

BACKGROUND OF THE INVENTION

Cross sectional imaging is an imaging technique which produces a large series of two-dimensional (2D) images of a subject, e.g., a human subject. Examples of cross sectional imaging techniques include computerized tomography (CT), magnetic resonance imaging (MRI), positron emission tomography (PET), SPECT scanning, ultrasonography (US), among others. A set of cross sectional images for a single patient, e.g., for different axially located cross-sections or for the same cross section at different times can be considered three dimensional (3D) image data, and even four dimensional (4D) image data for combinations of axial and temporal cross sectional images.

Various analytical approaches can be applied to the cross sectional images to detect and highlight portions of the patient's anatomy of interest. For example, the cross sectional images can be processed by segmentation, which generally involves separating objects not of interest from objects of interest, e.g., extracting anatomical surfaces, structures, or regions of interest from the images for the purposes of anatomical identification, diagnosis, evaluation, and volumetric measurements. In detecting tumor changes with therapies, volumetric measurement can be more accurate and sensitive than conventional linear measurements. 3D segmentation of cross sectional images provides a feasible way to quantify tumor volume and volume changes over time.

However, segmentation of primary and metastatic tumors, or certain organs (e.g., lungs, liver, spleen, and kidney), which can be highly heterogeneous, is challenging. Furthermore, segmentation of large and complex tumor masses, especially when they are attached to blood vessels and chest walls, as in lung lesions, can be challenging for the techniques currently available.

Identification of lymph nodes from cross sectional images can be important in diagnosing lymphoma. Lymphoma affects about 5% of all cancer cases in the U.S., and the American Cancer Society estimated that 79,190 Americans would be diagnosed with lymphoma in 2012. Enlarged lymph nodes are important indicators of cancer staging, and their size fluctuations can be used for therapy response assessment. The traditional uni-dimensional and bi-dimensional metrics can be based on the assumption that tumors change uniformly in all directions, which is not always the case. Volume as a biomarker can be a better biomarker than a uni-dimensional or bi-dimensional metric.

However, automated segmentation of the lymph node from cross sectional images remains challenging because its boundary can be unclear, its contrast with the background can be weak, and the surrounding structures can be of varying constitutions, e.g., in CT images, high density such as bone, low density such as fat, or similar density such as muscle.

There is a need for accurate and efficient delineation of these objects and measurement of their volumes, e.g., for better therapy response assessment, monitor organ regeneration after transplantation, and make non-invasive diagnoses in both clinical trials and clinical practice.

SUMMARY OF THE INVENTION

Techniques are provided for effective segmentation of organs and tumors and cells, even if such objects involve heterogeneous properties in cross sectional images. As used herein, the term voxel refers to an element of cross sectional images and is meant to refer to a picture element (pixel) of 2D image data as well as a volume element (voxel) of 3D image data as well as an element of any higher dimensional image data, unless a more restrictive meaning is evident from the context.

In a first set of embodiments, a method includes obtaining image data that indicates amplitude values at each of a plurality of voxels for a particular measurement modality. The method also includes determining an outer edge of a contiguous subset of voxels based on voxels that have an amplitude in a first amplitude range associated with a target object in image data of the particular measurement modality. The method also includes determining a center voxel, for which a center distance from the center voxel to a closest voxel of the outer edge is greater than a distance from any neighbor of the center voxel to a corresponding closest voxel of the outer edge. The method further includes determining a location and size of the target object in the image data based on the center voxel and the center distance.

In some embodiments of the first set, a gradient value is determined at a voxel. These embodiments include determining a reduced gradient equal to a product of the gradient with a fraction f that decreases with decreasing distance of the voxel from the center voxel.

In some embodiments of the first set, the method includes determining a refined boundary based on active contouring of an initial boundary based on at least one of the center voxel and the center distance or the watershed boundary. In some of these embodiments, the active contouring includes determining a change in boundary position based, at least in part, on an edge indicator function g that includes both a gradient and a Canny edge detector. In some of these embodiments, the active contouring includes determining a change in boundary position based, at least in part, on a potential well term weighted by a parameter $\alpha$. The potential well term comprises a product of a gradient of an edge detection function g and a gradient of a level set function $\phi$. In some of these embodiments, the active contouring includes determining a change in boundary position based, at least in part, on a volume preserving mean curvature term weighted by an independent parameter $\beta$. The volume preserving mean curvature term comprises a product of a magnitude of the gradient of the level set function $\phi$ and a difference between a local mean curvature $\kappa$ and a mean curvature for the boundary $\kappa_{mean}$.

In some embodiments of the first set, the method further includes determining based on a Markov model and on an amplitude range for background voxels and an amplitude range for part-solid voxels, whether a voxel outside and adjacent to a current boundary that is based on at least one of the center voxel and the center distance or the watershed boundary belongs to a background set or a first part-solid set. This embodiment also includes determining whether the voxel belongs to a solid tissue set or a second part-solid set based on a Markov model and on an amplitude range for solid tissue voxels and the amplitude range for part-solid voxels. The amplitude range for part-solid voxels overlaps on one end the amplitude range for solid tissue voxels and overlaps on the opposite end the amplitude range for background voxels. This embodiment further includes determining to move the current boundary to encompass the voxel if the voxel belongs to the first part-solid set and to the second part-sold set.

In a second set of embodiments, a method includes obtaining image data that indicates amplitude values at each of a plurality of voxels and determining a center of a region of interest in the image data. The method further includes determining a plurality of rays originating at the center in a corresponding plurality of directions in three dimensions and determining a plurality of adjacent rays for each ray. A series of amplitudes are determined at a corresponding plurality of distances from the center along each ray based on an amplitude of a nearest voxel to each distance from center of the corresponding plurality of distances from the center. An initial boundary is determined based on a path of minimum cost to connect one position on each ray to one position on each of a plurality of adjacent rays.

In some embodiments of the second set, determining the path of minimum cost includes minimizing a cost function that comprises a gradient cost and a homogeneity cost. The gradient cost decreases with increased radial gradient at a candidate point along a ray. The homogeneity cost increases with deviations in the amplitude along at least a portion of the ray between the candidate point and the center.

In some embodiments of the second set, the method also includes determining a refined boundary based on performing active contouring of the first boundary. In some of these embodiments, active contouring includes using an evolution equation that includes a first term and a second term. The first term indicates deviations in amplitude for all voxels inside the boundary from an average amplitude of all voxels inside the boundary. The second term indicates deviations in amplitude for local voxels outside the boundary from an average amplitude of the local voxels outside the boundary. The local voxels outside the boundary exclude a larger number of voxels outside the boundary.

In other sets of embodiments, a computer-readable medium causes an apparatus, or an apparatus or system is configured, to perform one or more steps of one or more of the above methods.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1B is a block diagram that illustrates scan elements in a 2D scan, such as one scanned image from a CT scanner FIG. 1C is a block diagram that illustrates scan elements in a 3D scan, such as stacked multiple scanned images from a CT imager or true 3D scan elements from volumetric CT imagers or ultrasound;

FIG. 2 is a flow chart that illustrates at a high level a method for determining a three dimensional boundary of a target tissue or object, according to an embodiment;

FIG. 3B is a flow chart that depicts an example method 330 for determining size and center of a target object and markers and gradients for a watershed transform to provide an initial boundary for the target object, according to an embodiment;

FIG. 8 is a block diagram that illustrates adjacency of example vertices on a sphere, and corresponding rays, according to an embodiment;

FIG. 10A is a two dimensional image that illustrates example three-dimensional image data mapped to two dimensions along a set of ordered rays, according to an embodiment;

FIG. 10B is a two dimensional image that illustrates example three-dimensional image data mapped to two dimensions along a set of ordered rays with a boundary determined, according to an embodiment;

DETAILED DESCRIPTION

A method, system, computer-readable medium and apparatus are described for segmenting solid or part-solid objects, such as lymph nodes and lung lesions. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of segmenting lung lesions or lymph nodes in CT scans. However, the invention is not limited to this context. In other embodiments other imaging modalities, such as MRI, magnetic resonance spectral imaging (MRSI), PET, SPECT, US, microscopy, cytometry imaging, among others, are employed, to accumulate 2D, 3D, 4D or higher dimensionality image data, for segmenting other solid or part-solid objects, such as other tissues, organs, tumors or cells. Such segmentation is called tissue detection herein.

1. Overview

Figure 1A:
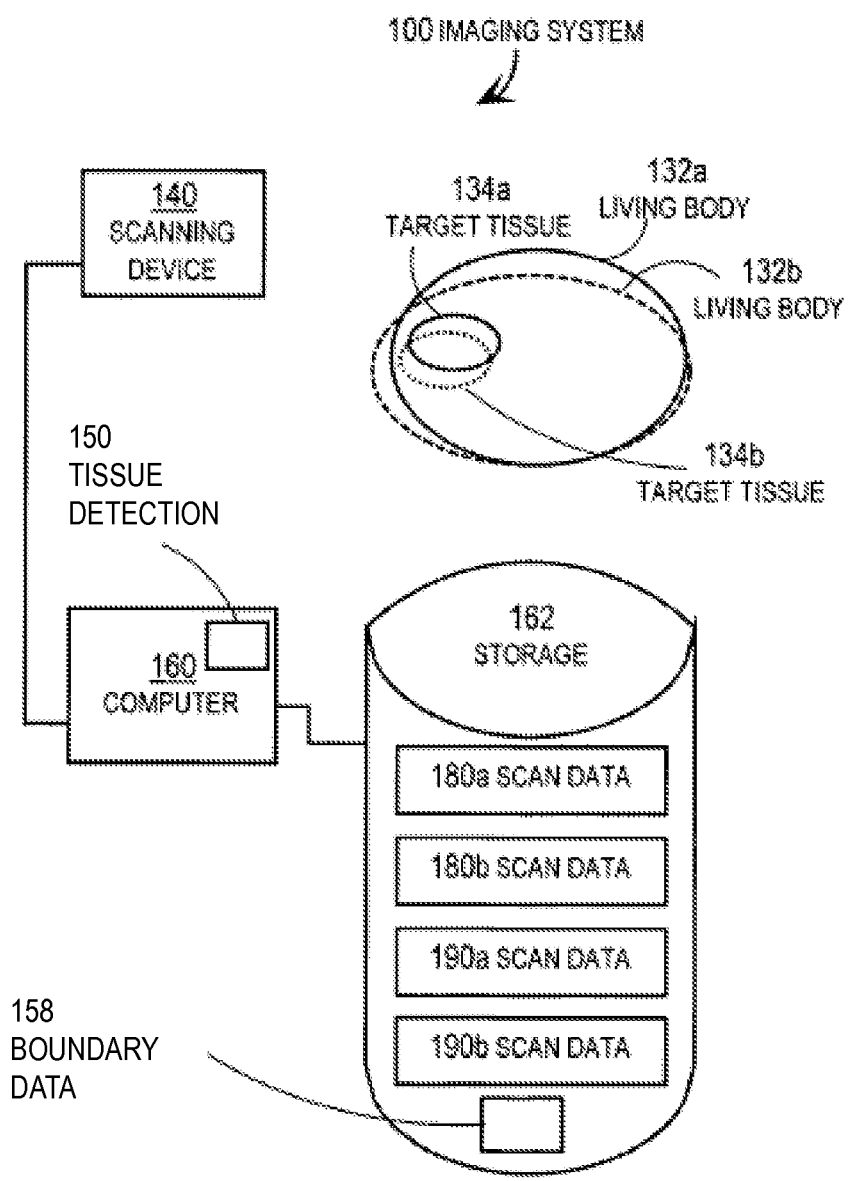
FIG. 1A is a block diagram that illustrates an imaging system for tissue detection, according to an embodiment.

FIG. 1A is a block diagram that illustrates an imaging system 100 for tissue detection, according to an embodiment. The system 100 is designed for determining the spatial arrangement of soft target tissue in a living body. For purposes of illustration, a living body is depicted, but is not part of the system 100. In the illustrated embodiment, a living body is depicted in a first spatial arrangement 132a at one time and includes a target tissue in a corresponding spatial arrangement 134a. At a different time, the same living body is in a second spatial arrangement 132b that includes the same or changed target tissue in a different corresponding spatial arrangement 134b.

In the illustrated embodiment, system 100 includes a scanning device 140, such as a full dose X-ray computed tomography (CT) scanner, or a magnetic resonance imaging (MRI) scanner, among others. In some embodiments, the scanning device 140 is used at one or more different times. The device 140 is configured to produce scanned images that each represent a cross section of the living body at one of multiple cross sectional (transverse) slices arranged along the axial direction of the body, which is oriented in the long dimension of the body.

In system 100, data from the imager 140 is received at a computer 160 and stored on storage device 162. Computer systems and storage devices like 160, 162, respectively, are described in more detail below with reference to FIGS. 12 and 13. Scan data 180a, 180b, 190a, 190b based on data measured at imager 140 at one or more different times or axial locations or both are stored on storage device 162. For example, scan data 180a and scan data 180b, which include scanned images at two slices separated in the axial direction, is stored based on measurements from scanning device 140 at one time. Scan data 190a, 190b, which include scanned images at two slices separated in the axial direction, is stored based on measurements from scanning device 140 at a different time.

In various embodiments, a tissue detection process 150 operates on computer 160 to determine a boundary between scan elements of scan data which are inside and outside a particular target tissue or cell. The boundary data is stored in boundary data 158 in associations with the scan data, e.g., scan data 180a, 180b, 190a, 190b.

Although processes, equipment, and data structures are depicted in FIG. 1A as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, although system 100 is depicted with a particular number of scanning devices 140, computers 160, and scan data 150, 160 on storage device 162 for purposes of illustration, in other embodiments more or fewer scanning devices, computers, storage devices and scan data constitute an imaging system for determining spatial arrangement of tissues, including cells.

FIG. 1B is a block diagram that illustrates scan elements in a 2D scan 110, such as one scanned image from a CT scanner. The two dimensions of the scan 110 are represented by the x direction arrow 102 and the y direction arrow 104. The scan 110 consists of a two dimensional array of 2D scan elements (pixels) 112 each with an associated position. Typically, a 2D scan element position is given by a row number in the x direction and a column number in the y direction of a rectangular array of scan elements. A value at each scan element position represents a measured or computed intensity or amplitude that represents a physical property (e.g., X-ray absorption, or resonance frequency of an MRI scanner) at a corresponding position in at least a portion of the spatial arrangement 132a, 132b of the living body. The measured property is called amplitude hereinafter and is treated as a scalar quantity. In some embodiments, two or more properties are measured together at a pixel location and multiple amplitudes are obtained that can be collected into a vector quantity, such as spectral amplitudes in MRSI. Although a particular number and arrangement of equal sized circular scan elements 112 are shown for purposes of illustration, in other embodiments, more elements in the same or different arrangement with the same or different sizes and shapes are included in a 2D scan.

FIG. 1C is a block diagram that illustrates scan elements in a 3D scan 120, such as stacked multiple scanned images from a CT imager or true 3D scan elements from volumetric CT imagers or MRI or US. The three dimensions of the scan are represented by the x direction arrow 102, the y direction arrow 104, and the z direction arrow 106. The scan 120 consists of a three dimensional array of 3D scan elements (also called volume elements and abbreviated as voxels) 122 each with an associated position. Typically, a 3D scan element position is given by a row number in the x direction, column number in the y direction and a scanned image number (also called a scan number) in the z (axial) direction of a cubic array of scan elements or a temporal sequence of scanned slices. A value at each scan element position represents a measured or computed intensity that represents a physical property (e.g., X-ray absorption for a CT scanner, or resonance frequency of an MRI scanner) at a corresponding position in at least a portion of the spatial arrangement 132a, 132b of the living body. Although a particular number and arrangement of equal sized spherical scan elements 122 are shown for purposes of illustration, in other embodiments, more elements in the same or different arrangement with the same or different sizes and shapes are included in a 3D scan.

The term voxels is used herein to represent either 2D scan elements (pixels) or 3D scan elements (voxels), or 4D or higher dimensional scan elements, or some combination, depending on the context.

Amplitude is often expressed as one of a series of discrete gray-levels. A grey-level image may be seen as a topographic relief, where the grey level of a voxel is interpreted as its altitude in the relief. A drop of water falling on a topographic relief flows along a path to finally reach a local minimum. Intuitively, the watershed of a relief corresponds to the limits of the adjacent catchment basins of the drops of water. For segmentation purposes, it is common to interpret the horizontal gradient of the grayscale image as elevation information. The horizontal gradient is expressed as a two element vector at each voxel, the magnitude and direction of the steepest increase in amplitude from the voxel to any of its neighbors. In various lattices, a voxel may have one, two, four, six, eight or more neighbors. Intuitively, a drop of water falling on a topographic relief flows towards the "nearest" minimum. The "nearest" minimum is that minimum which lies at the end of the path of steepest descent. In terms of topography, this occurs if the point lies in the catchment basin of that minimum. The length of that path weighted by the altitude drop is related to the topographical distance, as described in more detail below.

FIG. 2 is a flow chart that illustrates at a high level a method 200 for determining a three dimensional boundary of a target tissue or object, according to an embodiment. Although steps are depicted in FIG. 2, and in subsequent flowcharts FIG. 3, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. For example, in some embodiments, the method 200 includes a separate step for obtaining the image data that indicates amplitude values at each of a plurality of voxels for one or more cross-sectional slices or time frames or some combination. Any method may be used to obtain the image data, such as retrieving the data from the storage device 162, either locally or remotely, either in response to a request or unsolicited; or by performing the measurements by placing the living body into the imaging system 100 and operating the scanning device 140 and computer 160.

In step 201, a region of interest (ROI) is obtained. The advantage of an ROI is that large sections of the image data can be ignored during processing and the number of special cases that have to be handled by the processing is often greatly reduced. Any method may be used to obtain the ROI, including receiving data from an operator, either unsolicited or in response to a prompt, or retrieving a mask that indicates a one in voxels that are within the ROI and a zero elsewhere, from a storage device on a local or remote computer, at a fixed location or a location indicated by a user or program operating on a remote computer, either in response to a request or unsolicited. In some embodiments, the ROI is defined by a user, such as a radiologist viewing the images on a display device, e.g., by drawing using a pointing device (such as a computer mouse or touchscreen), on a reference slice of the images such that the ROI encloses the target tissue (such as a an organ or tumor) to be segmented. In various embodiments, the ROI includes both the target tissue and a portion of the background.

In some embodiments, the ROI is also generated by parameters provided by a user. For example, the user can specify a center on the reference image, and provide a pixel value and a radius, then a circular ROI is automatically generated. Similarly, an elliptical ROI, can be generated by providing the center of the ellipse and the lengths of its major and minor axes. ROI of other shapes can be generated in similar manner. In alternative embodiments, the ROI is automatically generated based on a number of selected points near a target boundary specified by the user. If the ROI does not enclose the target, it can be dilated to enclose the target, in response to further user commands. In some embodiments, an ROI is not involved; and, step 201 is omitted.

In step 203, object types in the ROI are classified, at least preliminarily. For example, it is specified that the target tissue is a particular organ or tumor therein, such as liver or brain or lung or lymph node. In some embodiments, the specification is made by a user in response to a prompt provided at a graphical user interface. In some embodiments, step 203 includes classifying one or more voxels within the ROI as one or more tissue types. For example, voxels that constitute a background to tissues of interest are classified as background voxels. Any method may be used to classify voxel during step 203. For example, prior knowledge as to the location or amplitude range of one or more target tissues or background are used to classify one or more voxels in the ROI. In some embodiments, cluster analysis of voxel amplitudes or amplitude statistics are used to classify one or more voxels during step 203. In an illustrated embodiment, step 203 includes step 205 to identify a part-solid tumor in the ROI, as described in more detail below with reference to FIG. 3. In some embodiments, classification of voxels as one or more tissue types is not involved; and, step 203 is omitted.

Steps 211 through 225 are directed to determining an initial position for one or more boundaries of a corresponding one or more target objects. In step 211, it is determined whether the initial boundary is to be determined in a two dimensional slice or a higher dimensional subset of the image data. In the illustrated embodiment, it is determined whether the initial boundary is to be determined in three dimensions or two. If two, then in step 213 one or more initial boundary curves in two dimensions are determined. For example in some embodiments, a user draws an initial boundary in or near the target tissue of interest. In other embodiments, the initial boundary is based on an approximate segmentation technique, such as a watershed method with internal and external markers. The watershed transform with internal and external markers is well known in the art and described, for example, in L. Vincent and P. Soille, "Watersheds in digital spaces: an efficient algorithm based on immersion simulations," *IEEE Transactions On Pattern Analysis And Machine Intelligence*, v. 13 (6), pp 583-598, June 1991. In some embodiments, the initial one or more boundaries are determined for a single subset of voxels in the image data, called a reference subset, such as on a reference slice at one axial position and moment in time. As used herein, a single slice of multiple slices at different axial positions or times or some combination is called a subset of the image data. A subset of the image data can also include other collections of voxels fewer than the entire set of voxels in the image data, whether on the same slice or same time frame or not.

In some embodiments an initial boundary is based on a center voxel and size of an object determined automatically in the image data. For example, image data that indicates amplitude values at each of a plurality of voxels for a particular measurement modality is obtained. Then, as described in more detail below, an outer edge of a contiguous subset of voxels is determined based on voxels that have an amplitude in a first amplitude range associated with a target object in image data of the particular measurement modality. A center voxel local to a center of the ROI is determined. A center voxel is a voxel for which a center distance from the center voxel to a closest voxel of the outer edge is greater than a distance from any neighbor of the center voxel to a corresponding closest voxel of the outer edge, A location and size of the object in the image data is determined based on the center voxel and the center distance.

In an illustrated embodiment, step 213 includes step 215 to use distance weighting of image gradients, as described in more detail below. In step 215, a gradient value is determined at each voxel within the center distance from the center voxel. Then, a reduced gradient is determined, in which the reduced gradient is equal to a product of the gradient with a fraction f that decreases with decreasing distance of a voxel from the center voxel. In the illustrated embodiment, the weighting is performed before applying the watershed transform or otherwise using gradients to segment a target object. That is, in some embodiments, a watershed boundary is determined based, at least in part, on the reduced gradient instead of the gradient at voxels within the center distance from the center voxel. This step offers the advantage of keeping structure, which is often found inside a target object, especially in lymph nodes, from affecting the outer boundary to be determined for the target object.

If it is determined in step 211 that the initial boundary is to be determined in three dimensions, then in step 220 a volume of interest (VOI) is determined. In the illustrated embodiment, the VOI is determined automatically based on the size of the ROI and the distance of the subset from the subset on which the ROI is defined, such as one slice. In other embodiments, the VOI is based, at least in part, on input received from a user.

In step 223, voxels within the VOI are sampled differently from the original voxels (are re-sampled). For example, in some embodiments the voxels in the VOI are super sampled by interpolating amplitudes at positions other than those in the original image data. In some embodiments, amplitudes from several voxels are grouped by selecting an average, median, maximum, minimum or some other statistic of the several voxels being grouped.

In another illustrated embodiment, the VOI is re-sampled in step 231 along rays emanating from a center voxel, such as a center voxel of a ROI used to define the VOI. Adjacency of rays is also determined, so that an initial boundary can be determined that does not change too much between adjacent rays. As described in more detail below, this also allows a 3-D segmenting problem to be recast as a 2-D segmenting problem that can be solved with fewer computational resources. Thus, during step 231, a center of a region of interest is determined in the image data; and, a plurality of rays is determined, wherein the rays originate at the center in a corresponding plurality of directions. Furthermore, a plurality of adjacent rays is determined for each ray. Then, a series of amplitudes at a corresponding plurality of distances from the center are determined along each ray based on an amplitude of a nearest voxel to each distance from center of the corresponding plurality of distances from the center.

In step 225, one or more initial boundary surfaces are determined in three or more dimensions. For example, in some embodiments a user draws an initial boundary in or near the target tissue of interest. In other embodiments, the initial boundary is based on an approximate segmentation technique, such as a watershed method with internal and external markers extended to three dimensions or more. In some embodiments, the three dimensional watershed transform also uses the reduced gradients near the center as indicated during step 215, above. In some embodiments, the initial one or more boundaries are determined for a single subset of voxels in the image data, called a reference subset, such as one or more of several slices along an axial position or at one or more moments in time.

The shape of the initial contour depends on the object to be approximated, and can be arbitrary to trace the boundary of the object on the reference image. Domain knowledge of the nature of the image and how it was taken can be relied upon for drawing the initial contour. The initial contour can also be generated automatically based on prior knowledge, such as anatomical position, in certain circumstances. The initial contour can be inaccurate for the true object boundary, and can be fully inside or fully outside the true object boundary, or can have intersections with the true object boundary. The initial contour can be drawn by an operator with a mouse or other input device. If the object of interest has multiple connected components (e.g., the left kidney and right kidney), the initialization can be realized by drawing multiple contours, each roughly enclosing the individual component, so that the multiple components can be segmented. The reference image can be selected based on the position of the image slice (e.g., in the middle of the cross sectional images for the tumor or organ) or an image in which the tumor or organ has a relatively large area.

In some embodiments using amplitudes along rays, step 225 includes step 233 to determine homogeiety costs among adjacent rays in the process of determining the initial boundary surface. In particular, a first boundary is determined based on a path of minimum cost to connect one position on each ray to one position on each of a plurality of adjacent rays. In an illustrated embodiment, described in more detail below, determining the path of minimum cost during step 233, includes minimizing a cost function that comprises a gradient cost and a homogeneity cost. The gradient cost decreases with increased radial gradient at a candidate point along a ray, while the homogeneity cost increases with deviations in the amplitude along at least a portion of the ray between the candidate point and the center. The portion is advantageously closer to the candidate point than to the center point, to avoid structure that may occur close to a center of a target object.

In step 241, the position of the one or more boundaries are refined using active contouring. Active contouring involves a moveable boundary where movement of the boundary is based on a differential equation called an evolution equation. In some embodiments, the evolution equation is a solution to a cost or energy minimization problem. For example, in some embodiments, the evolution equation is based on minimization of an energy functional that assigns a cost to properties of a boundary that deviate from desired properties for the boundary. A typical energy functional includes a cost for distance from a maximum gradient, a cost for lack of smoothness, or a cost for deviations from an average intensity on one or both sides of the boundary, among other terms. Any active contouring may be used. Thus, during step 241, a refined boundary is determined based on performing active contouring of a first boundary.

In some embodiments, using rays distributed in 3 dimensions or more, a hybrid global-local statistics terms are used in the evolution equations, as described in more detail below. That is, during step 242, performing active contouring of the first boundary comprises using an evolution equation that includes a global first term and a local second term. The global first term indicates deviations in amplitude for all voxels inside the boundary from an average amplitude of all voxels inside the boundary. The local second term indicates deviations in amplitude for local voxels outside the boundary from an average amplitude of the local voxels outside the boundary. The "local" voxels outside the boundary exclude a larger number of "non-local" voxels outside the boundary.

In other active contouring, e.g., performed in two or three dimensions on regular grids of voxels, rather than along radial rays, one or more of steps 243, 245, 247 or 249 are included. In step 243, active contouring of the initial boundary further comprising determining a change in boundary position based, at least in part, on an edge detection function g that includes both a gradient (such as a gradient based on a Gaussian Kernel) and a Canny edge detector, as described in more detail below. The Canny edge detector complements the gradient for gradually changing edges.

In step 245, active contouring of the initial boundary further comprises determining a change in boundary position based, at least in part, on a potential well term weighted by a parameter α, typically but not always greater than 1. The potential well term comprises a product of a gradient of an edge indicator function g and a gradient of a level set function φ that defines the current position of the boundary, and which drags the boundary change back when the change would cross the object boundary where φ=0.

In step 247, the active contouring of the initial boundary further comprises determining a change in boundary position based, at least in part, on a volume preserving mean curvature term weighted by an independent parameter β. The volume preserving mean curvature term comprises a product of a magnitude of the gradient of the level set function φ and a difference between a local mean curvature κ and a mean curvature for the boundary κmean.

In step 249, the active contouring of the initial boundary further comprises determining a change in boundary position based, at least in part, on a topographical distance term, (Li−Le). As described in more detail below, topographical distance L is a distance weighted change in amplitude; Li is a topographical distance to a boundary based on eroding the initial boundary by a plurality of voxels (e.g., to an internal marker of a watershed transform); and, Le is a topographical distance to a boundary based on dilating the initial boundary by a plurality of voxels (e.g., to an external marker of a watershed transform).

In step 251, it is determined whether the current boundary describes a special class of tissue that received particular, class-specific treatment. For example, in some embodiments, lung tissue, brain tissue and liver tissue receive class-specific treatments, either during definition of the initial boundary or during or after refinement. If so, then control passes to step 253. In step 253, class-specific operations are performed. In some embodiments, step 253 includes step 255 to determine the boundary of tissue, such as the liver or other organs, in which the boundaries are known to satisfy some intensity constraint or size and shape constraints (called topological constraints, herein) or position constraints, or some combination. In some embodiments, step 253 includes step 255 to expand the boundary for part-solid tumors based on a Markov model or step 257 to apply morphological operations, or both, as described in more detail below. In some embodiments, step 255 is only performed if it is determined that the target object likely involves sufficient part-solid tissue, e.g., during step 205, described above.

In step 255, it is determined whether a voxel outside and adjacent to a current boundary belongs to a background set or a first part-solid set based on a Markov model and on an amplitude range for background voxels and an amplitude range for part-solid voxels. The Markov model is used because the amplitude range for part-solid voxels overlaps on one end an amplitude range for solid tissue voxels and overlaps on the opposite end the amplitude range for background voxels. Step 255 also includes determining whether the voxel belongs to a solid tissue set or a second part-solid set based on a Markov model and on the amplitude range for solid tissue voxels and the amplitude range for part-solid voxels. The voxel is included within the tumor if it is classified as a part-solid voxel in both determinations. That is, it is determined to move the current boundary to encompass the voxel if the voxel belongs to the first part-solid set and to the second part-sold set. In some embodiments, the current boundary is based on the location and the size of the object. In some embodiments, the current boundary is based on the initial boundary using the watershed transform, with or without refinement by active contouring, as described above.

In step 261, it is determined whether there are to be any manual edits. For example, the current boundary is presented to a user along with a graphical user interface, which the user can operate to indicate a manual edit to be performed. If so, control passes to step 263 to receive commands from a user that indicate one or more manual edits to be performed. After manual editing, the edited boundary may be used directly or propagated to another subset or sent back for further refinement. For example, the user can use a pointing device to move a portion of the boundary, or mark a boundary as suitable for propagation in one or more directions to other or adjacent subsets of the image data. In the illustrated embodiment, the edited boundary is refined by passing the manually edited boundary back to step 241. In some embodiments, only a portion of the boundary in a vicinity of the user edits is included in the refinement during step 241, so step 263 includes determining a mask. The mask indicates where the current boundary may be refined (e.g., where the voxels of the mask hold a first value, such as "1") and where the current boundary may not be changed (e.g., where the voxels of the mask hold a different second value, such as "0").

In step 271, it is determined whether some stop condition is satisfied. For example, it is determined whether the entire volume of interest has been segmented. If so, the process ends. In some embodiments, the refinement-propagation is iterated for each slice within a volume of interest (VOI) until each slice of the VOI is processed. The VOI can be defined by the first and last images that enclose the entire object, and is specified in step 221. The propagation can also be terminated automatically using certain criteria, such as based on a pre-defined minimum size or intensity range of the segmented object on the current image, or the average intensity difference between the segmented object on a reference image (or on the previous image) and that on the current image.

If instead, it is determined in step 271 that manual input during step 263 indicates that a boundary is ready for propagation or that subsets of the image data within the volume of interest remained un-segmented, then the stop condition is not satisfied. If it is determined that a stop condition is not satisfied, then in step 273 the boundary is propagated to another or adjacent subset, such as the next slice in an axially displaced position or at the next moment of time. In some embodiments, the propagation is performed in two directions separately from the reference image: one towards the head direction and the other towards foot or toes direction. For example, the refined contour on one image can be projected on the next image in the propagation direction, which can be simply duplicated from the single previous slice, or based on the predication model based on all the previous segmentation contours. In some embodiments, the propagated contour is refined using a similar active contour method, e.g. by passing control back to step 241.

In some embodiments, step 273 includes propagating the boundary to the other or adjacent subset in such a way as to satisfy an intensity constraint, a typology constraint, or a position constraint, or some combination. For example, if the liver is being segmented, an intensity range associated with the liver is used to exclude any pixels or voxels within the boundary that fall outside the accepted intensity range. For example in CT data, liver tissue falls within a range from 0 to 2000 Hounsfield units (HU). Similarly, boundaries that form any shape or size outside the range expected for the target tissue in the current subset are excluded by the topology constraints. Furthermore, in some embodiments, boundaries that are positioned outside the range expected for a particular target tissue are also excluded.

After propagation to the next subset, the boundary or boundaries on the new subset, and not excluded by the constraints, are refined using active contouring, such as in step 241.

In some embodiments, the segmentation result is thus further analyzed to improve the accuracy of the result. Prior knowledge or available information about the objects, such as intensity range, position, or shape, are exploited and integrated into the method to improve the performance of the method. For example, regions having a statistical quantity of intensities exceeding a predetermined value or range can be excluded from the segmentation result.

In some embodiments, the described procedure also includes preprocessing the original set of image data to remove the portions of voxels or pixels not of interest in step 201. For example, for liver segmentation in CT images, the Hounsfield value of the pixel intensity can be used to preproccess the original images. Some organs (e.g., lung, fat or bone), have distinct Hounsfield range from the liver, and are separated by simple thresholding techniques. Thus, the techniques herein can integrate the above thresholding techniques into both segmentation and refinement process.

Prior knowledge or available information of the shape and position of the objects is also used, in some embodiments, to eliminate possible inaccuracies during propagation of the contour from one slice to another. For example, in the case of the liver, there is usually one connected component in the superior part of the liver. Therefore, during step 273, when the boundary is propagating towards the direction of the head, the connected components of the segmented results is first labeled and analyzed based on properties such as area or centroid. The labeled objects which has an area larger than a specified threshold and where the centroid falls into the specified range is selected as a candidate of true liver tissue. This, avoids, for example, the heart being mistaken as part of the liver. In the same fashion, when the boundary is propagating during step 273 towards the direction of the toes, the centroid of the connected components is used to exclude some of the non-target tissues; because, in the inferior part of the liver, the centroid of the contour often falls over the left side of the image. Additionally, the average intensity value in a labeled object, in some embodiments, is compared to the average intensity m of a reference image. The labeled object can be excluded if it is beyond a specified range.

3. Part-Solid Objects

Figure 3A:
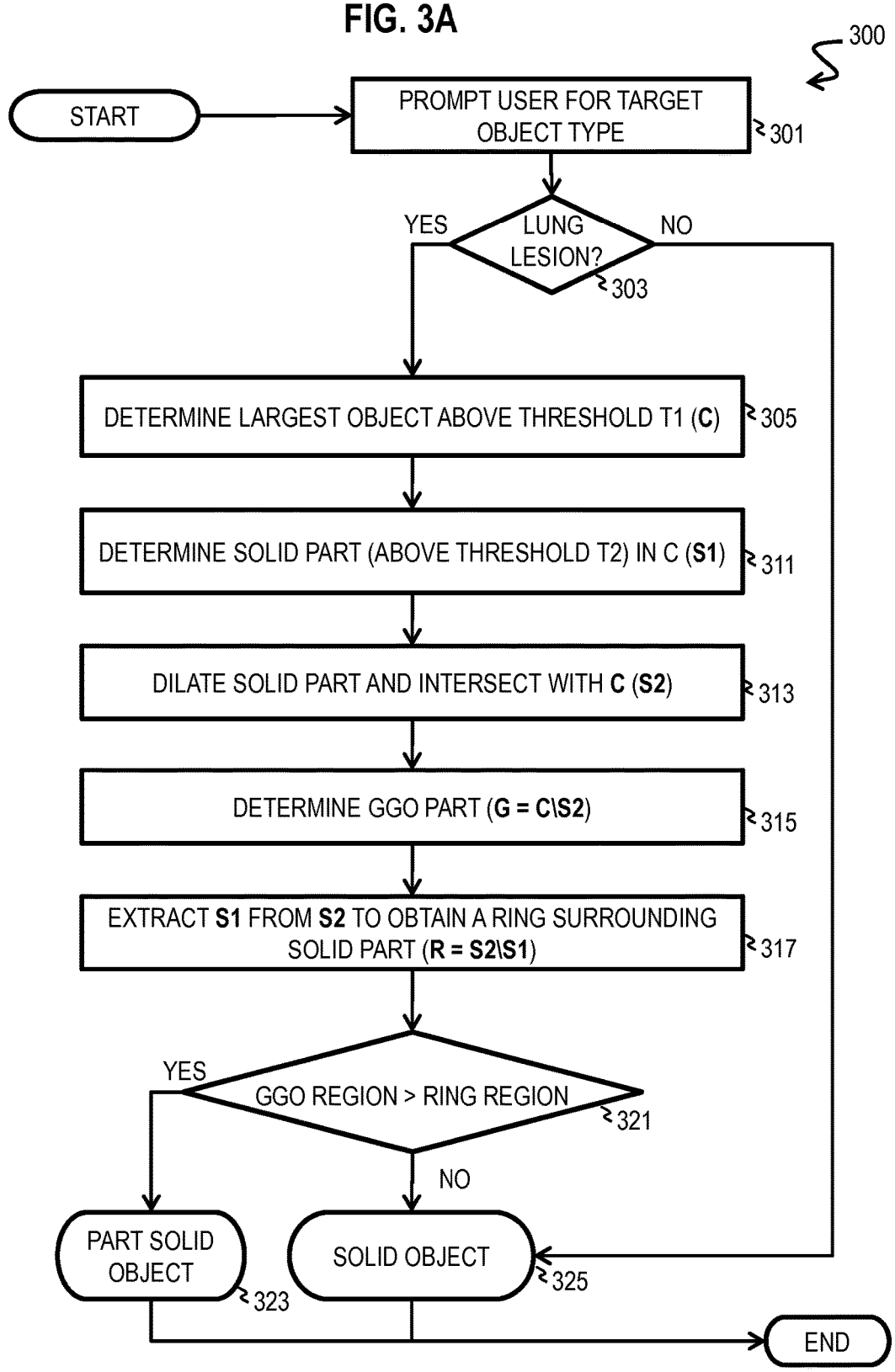
FIG. 3A is a flow chart that illustrates a method for performing one step of the method of FIG. 2 for determining if a target object is part solid, according to an embodiment.

FIG. 3A is a flow chart that illustrates a method 300 for performing one step 205 of the method of FIG. 2 for determining if a target object is part solid, according to an embodiment. In the illustrated embodiment, part-solid objects, such as some lung lesions, are a special class determined in step 251 to be subject to class specific operations in step 253, and specifically to part-solid specific operations in step 255.

In step 301a prompt is presented to a user to indicates the type of object to be segmented in the image data or ROI of the image data. In response, data is received that indicates the type of object to be detected or segmented or both. In step 303, it is determined whether the indicated type of object is one that may involve part-solid characteristics. If the type of object is one that may involve part-solid characteristics, such as the ground glass opacities (GGO) associated with some lung lesions, then control passes to step 305. Otherwise the object is determined to be solid in step 325 and not subject to processing as a part-solid object; and, the process ends.

In step 305, the largest object comprising voxels with amplitudes above a threshold T1 is determined. The voxels that belong to this object constitutes a set C of object voxels. In some embodiments the threshold T1 is associated with the type of object. For example, lung lesions in CT image data are associated with voxels that have amplitudes above a threshold T1 value selected in a range from about −800 HU to about −200 HU. In an illustrated embodiment T1 value is set to −500 HU. In some embodiments, step 305 includes forming a mask with values of one for every voxel above the threshold T1 and a value of zero for all other voxels. Morphological operations, such as dilation and erosion, are performed to remove holes and minor features. The number of voxels in each contiguous area with mask value one that remains is determined to identify the largest contiguous area with mask value one. Thus step 305 includes determining a first set C of contiguous voxels with amplitudes above a first threshold T1.

In step 311, a subset S1 of set C above a second, larger threshold T2 is determined to represent a solid part of the object. A value for T2 is selected in a range from about −200 HU to about 100 HU. In an illustrated embodiment, T2 is selected to be 0 HU. Thus, a first subset S1 of the first set C is determined, wherein the first subset S1 includes voxels with amplitudes above a second, larger threshold T2.

In step 313, a subset S2 of set C is determined by dilating subset S1 with a disk structural element of radius 2 pixels, and determining the intersection with set C. In step 315, a subset G of set C is determined by removing the subset S2 from the set C. In step 317, a ring R of set C is determined by removing the subset S1 from the subset S2. Thus, a ring R of voxels is determined in the first set C and outside the first subset S1 and adjacent to the first subset S1. As a consequence, the subset G comprises the voxels of C that are not in the subset S1 and not in the ring R. Thus steps 313 315 and 317 determine a subset G, wherein the subset G excludes the ring R and excludes the first subset S1.

In step 321, it is determined whether the subset G includes more voxels than the ring R, which indicates that the GGO region is greater than the ring region. If so, then the object is determined to be a part-solid object, and the process ends. If not, then the object is determined to be a solid object, and the process ends. Thus it is determined that the target object likely involves sufficient part-solid tissue if the number of voxels in the subset G is greater than the number of voxels in the ring.

If it is determined that the object is a solid object, then the boundary of the solid object is achieved after refining the initial boundary. If it is determined that the object is a part-solid object, then after refining the initial boundary, which produces a boundary for the solid portion of the object, additional step 255 is taken to expand the boundary to include the part-solid portion of the object.

4. Center and Size of Target Object

To perform a marker controlled watershed transform in two dimensions during step 213 or in three dimensions during step 225 to serve as an initial boundary, it is advantageous for the center and size of the object to be determined. In some embodiments, the center and size of the target object are determined automatically based on a simple ROI, which a user can easily supply during step 201 through a graphical user interface. In some embodiments, the ROI is also determined automatically, e.g., based on standard anatomy. It is advantageous that the ROI specified be roughly centered on the target object.

In some embodiments, the VOI is determined during step 221 based on the ROI as follows. If an elliptical ROI that encloses the lesion is centered at $O_o$ with semi-major axis a and semi-minor axis b, then, in an illustrated embodiment, the VOI is a box that encompasses the ellipse in the X-Y plane and encompasses the slices within a distance equal to (a+b)×pixel spacing from the reference slice along the Z-axis in both the head and foot directions.

In step 223, in some embodiments, the VOI is isotropically super-sampled to the in-plane resolution. The subsequent image processing techniques described in some embodiments are automatically performed on the super-sampled VOI dataset.

During step 213 in two dimensions or step 225 in three dimensions, in embodiments that perform the marker-controlled watershed method, the marker for the lesion and non-lesion (or background) are determined. One method involves finding an amplitude threshold that separates the target object (e.g., a solid lung lesion) from the background (e.g., the lung parenchyma), and using distance transform to find a center of the voxels associated with the target object. The background markers are determined from the surrounding voxels and the region outside the VOI. FIG. 3B is a flow chart that depicts an example method 330 for determining size and center of a target object and markers and gradients for a watershed transform to provide an initial boundary for the target object, according to an embodiment.

In some embodiments, a Gaussian mixture model is used to determine the threshold that separates the target object from the background. Because the ROI contains both target object (e.g., lung lesion) and background (e.g., lung parenchyma) voxels, amplitude distribution of the voxels can be modeled by two Gaussian distributions P(A|target) and P(A|background), where A is the voxel amplitude. The mean values and variations of the two Gaussian distributions are estimated in step 331, e.g., by the Expectation-Maximization method. The proportions of object P(target) and background P(background) are also estimated during step 331 by the relative areas under the two Gaussian curves. Given amplitude A for a pixel, the probability of that pixel belonging to class "Q" can be derived as follows: P(Q|A)=P(A|Q) P(Q)/P(A), where Q can be target or background. According to the Bayesian decision theory, a voxel with amplitude A can be classified as a target voxel if the a posteriori probability P(target|A) is greater than P(background|A). Thus, the target object threshold Ttarget is determined in step 333 using Equation 1.

$$P(T\text{target}|\text{target})P(\text{target})=P(T\text{target}|\text{background})P(\text{background}) \quad (1)$$

In step 335, the voxels inside the target object are determined. In some embodiments it is known that target object voxels belong to a particular one of the two Gaussian models and therefore are known to have amplitudes above or below the threshold Ttarget. If it is uncertain which of the two Gaussians represents the target object, then the amplitudes at the center of the ROI or VOI are assigned to the target object and voxels with amplitudes on the same side of the threshold Ttarget are considered voxels inside the target object.

In step 337, all voxels inside the target object are given a binary image value of 1 and all those outside are given a binary image value 0. In some embodiments, step 337 includes morphologically opening the binary image to remove noise and then closing the opened image so as not to miss small pieces that may belong to the target object. Holes inside the largest object are filled in the process.

In step 339, the distance of each voxel within the target image threshold to the nearest edge (e.g., nearest background voxel) is determined, e.g., by performing a distance transform on the binary image. The voxel O that has the local maximum value on the distance map is called the center voxel. The center voxel O is reached, in some embodiments, by walking from the center of the ROI, $O_o$, to its neighbors with the largest distance value; and repeating the process until the local maximum is reached. The distance $\hat{R}$ of the center voxel O corresponds to the radius of the maximum inscribed circle centered at the point O. A circle that is centered at O with a radius $\hat{R}$ can be taken as the estimated size and location of the target object. The center voxel and $\hat{R}$ are determined during step 341.

5. Modified Watershed Method

The estimated object location and size is used, in some embodiments, in a modified watershed method as follows. As the watershed surfaces can be attracted by spurious edges far from the object boundary, the object marker is advantageously located in proximity to the background markers; and, it is further advantageous to suppress non-object edges in the object marker. To accomplish this, in step 343, the object marker (interior marker for the marker controlled watershed method) is chosen as a circle centered at the center voxel O with a radius of smaller than $\hat{R}$, e.g., in a range from about 0.1 $\hat{R}$ to about 0.9, or about 0.5 $\hat{R}$ in some embodiments. In some embodiments, during step 345, the ROI is applied to each slice of the VOI, and pixels outside the ROI are considered background markers. When the object is a lung lesion, large regions with amplitudes of typical lung parenchyma (e.g., density less than −800 HU in CT images) or high amplitude regions (e.g., density greater than 200 HU in CT images) are also considered background markers.

While in an ideal situation the target object boundary is the only edge in the image, in reality there are often edges within internal (object) and external (background) markers other than the object boundary. In step 347, these edges are suppressed by reducing the gradient of the original image, e.g., by multiplying the gradient image by a bowl-shaped function f(r):

$$f(r) = \{r/(\gamma\hat{R})\}^2 \quad \text{if } r < \gamma\hat{R} \quad (2)$$
$$= 1 \quad \text{if } r \geq \gamma\hat{R}$$

where r is the distance of each voxel to the center voxel O, and γ is a parameter selected in a range from about 0.4 to about 1.2. In three dimensions, the function is smaller than 1 inside the sphere of the radius $\hat{R}$ and equal to 1 outside the sphere. In two dimensions, the function is smaller than one inside the circle of radius $\hat{R}$ and equal to one outside the circle. Inside the sphere, or circle, the function is proportional to the square of the radius from the center. To calculate the Euclidean distance at each voxel in the VOI to the center O, a distance transform method can be employed. In some embodiments, the distance transform perform during step 339 is retained in use for the purposes of equation 2 during step 347.

In some embodiments, the gradient image is further modified by morphological reconstructions so that the markers are the only local minimums on the gradient image. By using markers and suppressing edges close to the center of the object, a 2D or 3D watershed surface can be obtained, in step 215 or step 225, respectively, as the initial boundary. Then the watershed boundary can be found using any watershed formation available, such as using an immersion method, e.g. a method described by Vincent L., & Soille, P. (1991).

In some embodiments, the watershed boundary is close to the target object boundary. However, parts of the surrounding structure, such as vessels, can also be segmented as part of the target object. To refine the watershed surface, in some embodiments, a morphological opening operation is carried out with a spherical structural element. In some embodiments, the radius of the spherical structural element is selected to be a predetermined value, such as a fraction of the center distance $\hat{R}$. In some embodiments, the fraction is chosen to be in a range from about 0.1 $\hat{R}$ two about 0.5 $\hat{R}$, e.g., about 0.3 $\hat{R}$. The largest connected component after this morphological opening operation can be taken as a rough segmentation of the target object. In some embodiments, the radius is taken to be no more than the largest radius of typical vessels, say 4 pixels.

6. Improved Active Contouring for Watershed Boundary

While the morphological operation can remove some undesired anatomical structures that attach to a target object, it can also remove the surface detail of the target object. Therefore, in some embodiments, a watershed surface is further refined by an active contour method that smoothes the initial boundary while honoring the edge detail near the boundary.

In one embodiment, the active contour method used to refine the watershed surface includes using a geometric active contour model. Though models such as Chan-Vese, local region based active contours, explicit snake, and Gradient Vector Flow can be used, they can evolve to irregular shape and can be difficult to compute or can converge slowly. A modified geometric active contour model is used in some embodiments because the initial contour is often close to the true boundary and the level set representation can make it easy to add more constraints.

In a level set representation, voxels enclosed by a boundary have values less than a level set value and voxels outside the boundary have values greater than the level set value. In many embodiments, the level set value is zero and the values assigned to other voxels are related to the distance of that voxel to the boundary properly signed to be negative inside the boundary and positive outside the boundary. In level set representation, the model deforms an initial curve to minimize a weighted length in two dimensions (or weighted surface area in three dimensions) of the boundary. The weighted length or surface area of the boundary is given by Equation 3.

$$\varepsilon(\phi) = \int g \delta(\phi) |\nabla \phi| dxdydz \qquad (3)$$

where φ is the level set representation of the curve, δ B is the Dirac delta function, and g is an edge indicator function, which is a positive and decreasing function of the gradient, and that, in some embodiments, has the form of Equation 4a.

$$g = \frac{1}{1 + \left(\frac{\nabla G_\sigma * I}{N}\right)^2} \qquad (4a)$$

where I(x) is the image amplitude at position x, $G_\sigma$ is a Gaussian Kernel with standard deviation σ, the ∇ symbol is the gradient operator, the asterisk "*" denotes convolution, and N is a normalization term that takes on the mean value of the smoothed gradient.

The gradient detector of Equation 4a is good for strong edges, but for gradually changing edges, a thick band of voxels exhibit a locally maximum gradient. Thus, using Equation 4a, the active contour result that reduces curvature, as described below, is often smaller than desired due to the curvature reduction term. A Canny edge detector can localize edges better, though the edges often do not form a closed curve. A new edge indicator function g that combines both edge detectors is used in some embodiments, as given by Equation 4b.

$$g = \frac{1}{1 + \left(\frac{\nabla G_\sigma * I}{N}\right)^2} 0.5 + (1 - Gcanny)0.5 \qquad (4b)$$

Where Gcanny is 1 if position x is an edge point and 0 otherwise. Using non-maximum suppression and hysteresis thresholding, Canny edge detector yields one at edge points and zero otherwise, which has the property of good detection, good localization and minimal response (Canny 1986).

Figure 3C:
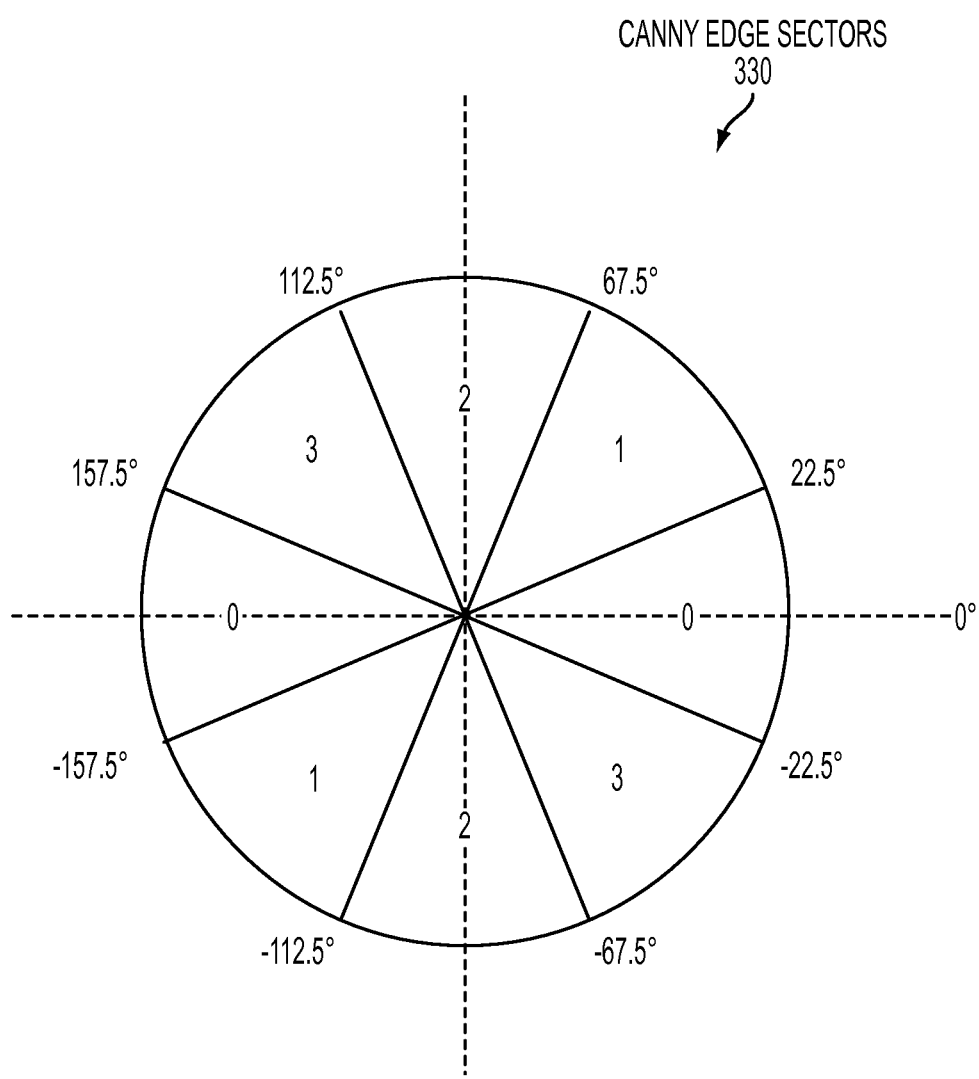
FIG. 3C is a block diagram that illustrates Canny sectors, used in some embodiments.

Canny edge detector consists the following steps. A. Smooth the images with a Gaussian filter. B. Compute the gradient orientation and magnitude. Gradient operators, e.g., Sobel operators, in x and y direction were applied to obtain the gradient in x and y direction (Gx and Gy) respectively. The magnitude of the gradient is approximated by $\sqrt{(G_x)^2 + (G_y)^2}$, and the orientation is calculated using A TAN(Gy, Gx). C. The edge direction is assigned to one of four sectors (0, 1, 2, 3) as depicted in FIG. 3C. D. To localize the edge position, especially for gradually changing edges, non-maxima edge responses were suppressed by taking the points whose magnitude are locally maximum in the direction of the gradient. For example, if the edge direction is in zone 0, then an edge pixel must have a magnitude greater than the pixels in the north and south directions. E. Hysteresis is applied to eliminate gaps. Two thresholds (T_HIGH and T_LOW) were used. First pixels in the non-maxima suppressed image that are above T_HIGH are considered edge pixels, and pixels that are above T_LOW and are connected to edge pixels are considered edge pixels too.

In some embodiments, for calcified lesions, the CT density is clamped to be no higher than 300 HU prior to the gradient calculation in the geometric active contour step.

Minimizing ε(φ) results in the following gradient flow according to the Euler-Lagrange equation:

$$\phi_t = g\delta(\phi)\kappa + \nabla g \cdot \nabla \phi \frac{\delta(\phi)}{|\nabla \phi|} \quad (5)$$

where κ is the local mean curvature defined as $$\kappa = div\left(\frac{\nabla(\phi)}{|\nabla \phi|}\right),$$

and δ(φ) can be replaced by |∇φ| therefore Equation 5 can be rewritten as:

$$\phi_t = g\kappa|\nabla\phi| + \nabla g \cdot \nabla\phi \quad (6)$$

The first term of Equation 6 is a mean curvature flow weighted by the edge indicator function. The second term acts as a potential well, which drags the surface back when it crosses the object boundary. When the potential well is not deep enough to prevent the surface from passing through the boundary, the strength of the potential well can be increased by increasing its coefficient term a as in Equation 7:

$$\phi_t = g\kappa|\nabla\phi| + \alpha\nabla g \cdot \nabla\phi \quad (7)$$

To regulate the shape of the contour, a volume preserving mean curvature flow technique is also employed, in some embodiments. The mean curvature flow is the evolution of a curve by $\phi_t = \kappa|\nabla\phi|$, which is the fastest way to minimize the perimeter (surface area) of an object. By subtracting the mean curvature as in the Equation 8, $$\phi_t = (\kappa - \kappa_{mean})|\nabla\phi| \quad (8)$$

a boundary will evolve to a round one while preserving the volume. When the boundary is a circle, the right term in the above equation is zero and the boundary will stop evolving due to this term.

With a weighted potential well and volume preserving mean curvature flow, the evolution equation, in some embodiments, is given by Equation 9.

$$\phi_t = g\kappa|\nabla\phi| + \alpha\nabla g \cdot \nabla\phi + \beta(\kappa - \kappa_{mean})|\nabla\phi| \quad (9)$$

where α and β are fixed values. To enhance the potential well, α is often selected to be greater than one. The values for parameters α and β are selected from a range of about 0 to about 50, and preferably in a range from about 1 to about 20. In some embodiments, α and β are each selected as 10.

In some embodiments, the watershed method and the active contour method are directly coupled to segment an anatomical object, e.g., by minimizing an energy functional when the watershed method is being carried out, such that the result of the watershed method, i.e., the curve or surface of the 2D or 3D anatomical object, has a smooth boundary. The topographical distance of a point x to a basin (marker M) is the shortest distance traveled on a relief image from voxel p to any voxel q in the basin. The watershed line is the set of points equidistant to two or more markers. The topographical distance can be computed using shortest path algorithms, such as described by Meyer 1994. In such embodiments, it is convenient to represent the level set function by a signed distance function (SDF) to overcome problems of numerical stability. In one embodiment, the energy functional of the watershed method takes the form of Equation 10.

$$E(\phi) = \int D_i H(\phi) + D_e (1 - H(\phi)) dxdydz + \lambda \int \delta(\phi)|\nabla\phi|dxdydz \quad (10a)$$

where $D_i$ and $D_e$ (also called Li and Le, respectively, below) are the topographical distances from each point to internal and external markers (also called basins or catch basins) respectively. φ(x, y, z, t) is the level set function, where (x, y, z) is the point location and t represents iteration step, and H(•) is the Heaviside function. The energy functional in this embodiment is minimized by means of the gradient descent given by Equation 10b.

$$\frac{\partial \phi}{\partial t} = -\frac{\partial E}{\partial \phi} = \delta(\phi)(D_i - D_e) + \lambda\delta(\phi)\nabla\left(\frac{\nabla(\phi)}{|\nabla\phi|}\right) \quad (10b)$$

Recall that to perform the watershed method, internal and external markers are first determined. For example, a ROI of elliptical or circular shape can be defined by a user or operator on a reference slice such that the ROI surrounds. From the center of the circle, an internal marker is obtained, in some embodiments, using a small balloon force with a smoothness constraint. Here a balloon force is a force that moves the contour outward along the normal of the surface, i.e., $$\frac{\partial \phi}{\partial t} = -v\vec{n} = -v\frac{\nabla\phi}{|\nabla\phi|},$$

where v is the strength of the force. A VOI is generated based on the ROI for a 3D watershed transform. External marker outside space of the VOI are obtained using any of several methods, as described elsewhere herein.

Thus, in some embodiments, the evolution equation is modified to incorporate the topographical distance from the interior and exterior markers so that the refined boundary properly honors the watershed line. In some embodiments, the evolution equation also includes a term to minimize the perimeter (or surface area) of the boundary. The resulting evolution equation with all these terms is $\phi_t(x)$=geometric term+strengthened potential well term+volume preserving mean curvature flow term+topographic distance term+term to minimize the length of the contour. This evolution equation is given by Equation 11.

$$\begin{aligned}
\phi_t(x) = &\, g(x)\kappa(x)|\nabla\phi(x)| + &&\{\text{geometric term}\} \quad (11)\\
&\alpha\nabla g(x) \cdot \nabla\phi(x) + &&\left\{\begin{array}{l}\text{strengthened potential well}\\ \text{term}\end{array}\right\}\\
&\beta(\kappa(x) - \kappa mean)|\nabla\phi(x)| + &&\left\{\begin{array}{l}\text{volume preserving mean}\\ \text{curvature flow term}\end{array}\right\}\\
&\gamma(Li - Le)|\nabla\phi(x)| + &&\{\text{topographical distance term}\}\\
&\lambda\nabla \cdot (\nabla\phi(x)/|\nabla\phi(x)|)|\nabla\phi(x)| &&\left\{\begin{array}{l}\text{boundary length}\\ \text{minimization term}\end{array}\right\}
\end{aligned}$$

Where γ and λ are constants chosen to provide acceptable performance, φ(x) is the level set function, g(x) is the edge indicator function, κ(x) is the curvature of the level set function, κmean is the mean curvature at the level set, Li is the topographical distance to a boundary based on eroding the initial boundary by a plurality of voxels (e.g., to an internal, object, marker of a watershed transform); and, Le is a topographical distance to a boundary based on dilating the initial boundary by a plurality of voxels (e.g., to an external, background, marker of a watershed transform) and negating the binary mask so that only outside voxels are considered. In various embodiments, the degree of dilation or erosion or both is determined by the size of the initial segmentation result Topographical distance is computed based on the gradient of the image data at each voxel.

The topographical distance L between two voxels x and y is a spatial weighted distance defined by Equation 11a, where inf refers to the infimum (i.e., greatest lower bound) of a set.

$$L(x, y) = \inf_{\gamma \in [x \to y]} \int_\gamma |\nabla f(\gamma(s))| ds \quad (11a)$$

where [x→y] denotes the set of all possible paths from voxel x to voxel y. In discrete case, the topographical distance between two voxels p and q is a weighted distance defined by Equation 11b.

$$L(p, q) = \min_{\pi \in [p \to q]} \sum_{i=1}^{n} cost(p_{i-1}, p_i) \quad (11b)$$

where the minimization is taken over all possible paths $(p_1=p, p_2, \ldots, p_n=q)$ between two voxels p and q (See Meyer, F. 1994). The cost of walking from voxel p to voxel q is related to the lower slope, which is defined as the maximum slope linking p to any of its neighbors of lower altitude. Thus the cost is given by Equation 11c.

$$cost(p_{i-1}, p_i) = \begin{cases} LS(p_{i-1}) \cdot dist(p_{i-1}, p_i) & \text{if } f(p_{i-1}) > f(p_i) \\ LS(p_i) \cdot dist(p_{i-1}, p_i) & \text{if } f(p_{i-1}) < f(p_i) \\ \min(LS(p_i), LS(p_{i-1})) \cdot dis(p_{i-1}, p_i) & \text{if } f(p_{i-1}) = f(p_i) \end{cases} \quad (11c)$$

where dist( ) denotes the Chamfer distance, and LS(x) is the lower slope at point x.

When the evolution stops, the object voxels in three dimensions are taken as the region with $\phi(x, y, z) \leq 0$, and the boundary as voxels where $\phi(x,y,z)=0$, where x, y, z here refer to spatial coordinates of each voxel. In two dimensions, the object is taken as the region with $\phi(x,y) \leq 0$, and the boundary as voxels where $\phi(x,y)=0$. This boundary can be propagated to the next slice, if any during step 273. The VOI can then be sub-sampled back to its original resolution. The volume of the object can be derived by multiplying the number of voxels of the object and the voxel volume. As previously noted, if the object is determined to be part-solid, then the embodiments previously described in this section may segment only the solid part, leaving part of the GGO region(s) as background. This shortcoming is corrected in step 255, described next.

7. Class Specific Operations for Part-Solid Objects

Part-solid objects often appear in image data, e.g., in CT image data as regions of ground glass opacities (GGO). GGO, or other part-solid, regions are included in the segmentation in some embodiments, using a Markov random field (MRF) model. This process can be understood through the following considerations, but the method is not limited by the accuracy or completeness of this treatment.

The image Y is viewed as an observation of a label field X degraded by noise (which may be assumed to be Gaussian for simplicity). The label field is assumed to have Markov property, namely each random variable in the field only directly depends on its neighboring variables. The maximum a posteriori estimation of the label field X* is the label field that most likely generates an observation of Y, i.e.

$$X^* = \arg\max_X P(Y \mid X).$$

When the label field is binary, X* can be solved exactly by converting the problem to a maximum flow problem, which can be solved by a fast graph cut algorithm.

The voxel amplitudes (e.g., densities in CT images) are considered to be taken from three Gaussian distributions: one representing the background (e.g., normal lung parenchyma), another representing part solid regions, such as the GGO regions, and the third representing solid regions (e.g., high density regions in CT images) such as solid tumor, vessels, muscles, etc. In general, the ranges of amplitudes in these distributions overlap. The amplitude range for part-solid voxels overlaps on one end the amplitude range for solid tissue voxels and overlaps on the opposite end the amplitude range for background voxels. For example, in CT images, the mean and standard deviation for the density distribution of lung parenchyma can be taken as −900 HU and 200 HU, those of GGO regions can be taken as −400 HU and 200 HU, and those of high density regions can be taken as 50 HU and 100 HU. The parameters can also be individually estimated for each object from the density statistics in the VOI.

In some embodiments, instead of solving a label field with three labels, two binary label fields can be solved: one label field with background label and part-solid label (e.g., with a lung parenchyma label and a GGO label), and the other label field with part-solid label and a solid label (e.g., with a GGO label and a high density label). The part-solid voxels in the first label field also includes solid-voxels; and, the part-solid voxels in the second label field also includes background voxels. For example, the "GGO region" in the first label field also includes high density region(s); and, the "GGO region" in the second label field also includes normal lung parenchyma. The intersection of the two part-solid labeled regions is used as final part-solid region (e.g., the final GGO region). In some of these embodiments, the boundary for the object is extended to encompass the voxels labeled as part-solid. Segmentation by the above MRF model can separate the VOI into background (e.g., low density lung parenchyma) and solid (e.g., high density regions).

As usual, other constraints can be used in step 201 or step 203 or step 253 or step 263 or step 273 to excludes some voxels from consideration or propagation. For example, in some embodiments related to lung lesions, voxels with CT density denser than −100 HU can be excluded as they are likely vessels or part of the chest wall.

8. Example Refined Watershed Embodiment for Lung Lesions

Figure 4A:
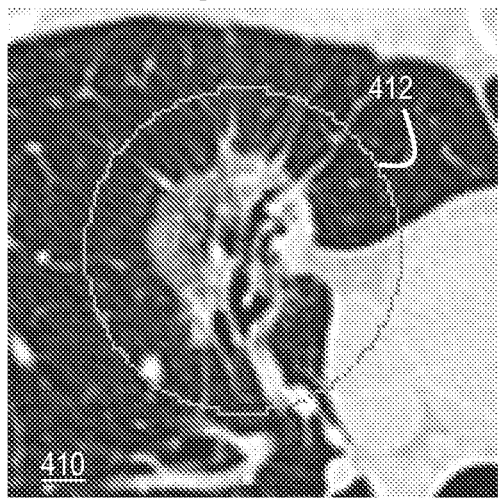
FIG. 4A through FIG. 4G are images that illustrate example steps of the method of FIG. 2 for segmenting a lung lesion, according to an embodiment.

FIG. 4A through FIG. 4G are images that illustrate example steps of the method of FIG. 2 for segmenting a lung lesion, according to an embodiment. FIG. 4A is an image 410 of a lung lesion in one slice of CT image data. A region of interest 412 is indicated as a circle (ellipse with semi-major and semi-minor axes equal).

As described above, in step 221, the VOI is a box that encompasses the ellipse in the X-Y plane and encompasses the slices within a distance equal to (a+b)×pixel spacing from the reference slice along the Z-axis in both the head and foot directions. In step 223, the VOI is isotropically super-sampled to the in-plane resolution. The subsequent image processing techniques described below are automatically performed on the super-sampled VOI dataset.

Figure 5:
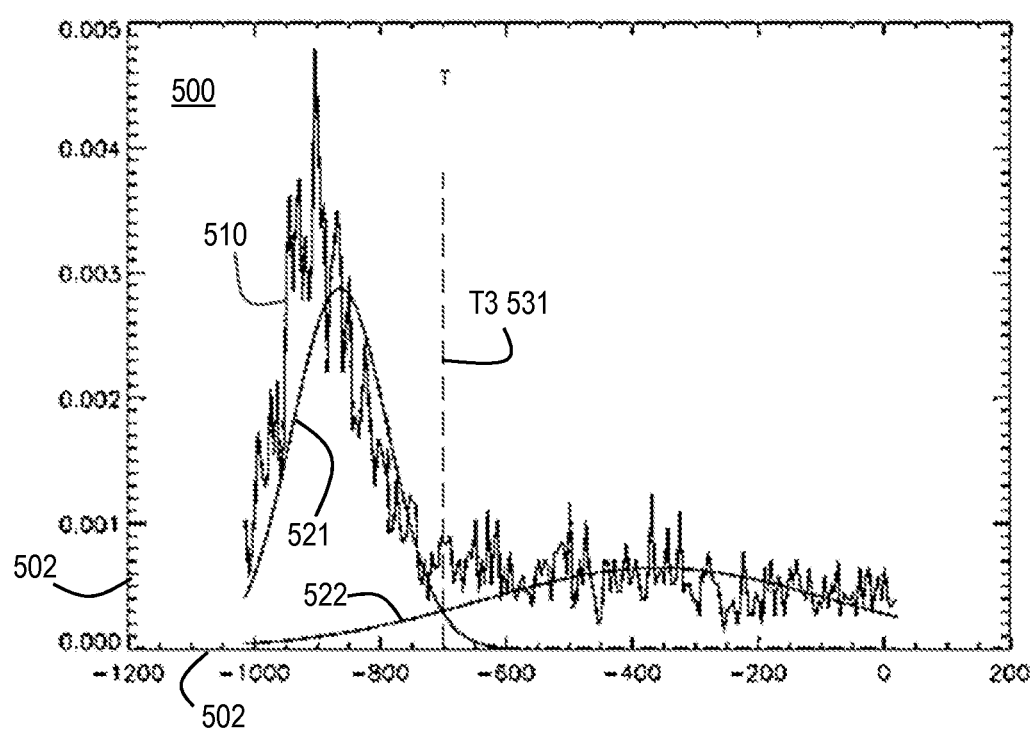
FIG. 5 is a graph that illustrates example dual-Gaussian fit to amplitude histogram in a set of voxels, according to an embodiment.

A threshold is determined for the lung lesion according to steps 331 and 333 described above with respect to FIG. 3B. FIG. 5 is a graph 500 that illustrates example dual-Gaussian fit to amplitude histogram in a set of voxels, according to an embodiment. The horizontal axis 502 is amplitude bin in HU units for CT density (less dense voxels have lower density values that are more negative on this axis on which water has a value of zero and air −1000). The vertical axis indicates the percent of voxels that fall in each amplitude bin. The amplitude distribution is given by trace 510. In the image 410, the more dense voxels are lighter and the less dense voxels are darker. A dual Gaussian fit determines a first Gaussian trace 521 representing one type of tissue (e.g., background=lung parenchyma); and, a second Gaussian trace 522 represent a second type of tissue (e.g., target object that is lung lesion). Voxels with densities above threshold T3, e.g., line 531 in FIG. 5 at about −700 HU, are considered (solid) lung lesion voxels for initial thresholding purposes. In some embodiments, voxels with CT densities above −700 HU are known to be lung lesions. In other embodiments, voxels with CT densities above −700 HU are determined to be lung lesion voxels because the voxels at the center of the ROI 412 have densities above −700 HU.

Figure 4B:
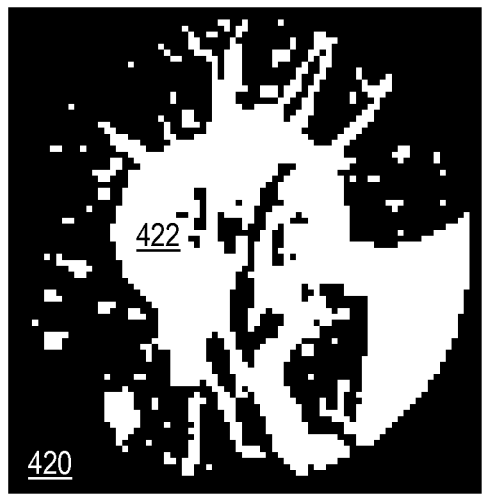
Figure 4C:
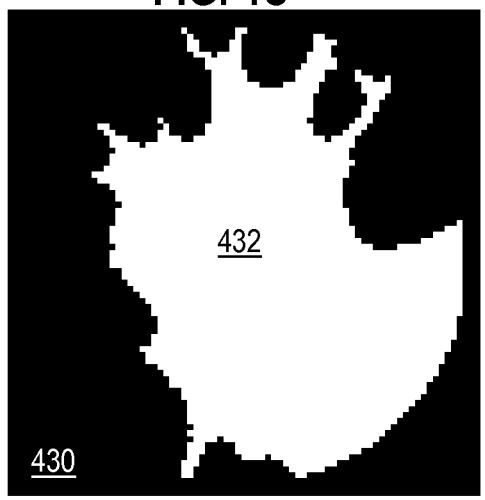

Step 337 is demonstrated by FIG. 4B and FIG. 4C. FIG. 4B is a binary image 420 that illustrates an example result of thresholding based on a dual Gaussian fit to amplitudes in a ROI, according to an embodiment. Only voxels inside the ellipse ROI are included. Here the threshold is −700 HU, and voxels 422 with higher densities, above −700 HU, are indicted by the value 1 (white) and the others are indicated by the value 0 (black), as are voxels outside the ROI.

FIG. 4C is a binary image 430 that illustrates an example result of morphological operations, according to an embodiment. Small holes are filled and the boundary is smoothed. In this example, each voxel with binary value 1 is dilated, that is, the value 1 is assigned to all voxels within a number n of voxels centered on the voxel. This tends to move the boundary outward. The dilation is followed by an erosion of the same number of voxels. For example, the value 0 is assigned to all voxels within a number n of voxels centered on a voxel with a value of 0. Voxels 432 have value 1 and represent a region that includes the target object, which in this embodiment is the target lung lesion In some embodiments, the average density inside the object (voxels 422 or 432) is used to determine whether the object is part solid or not during step 205, moved in this embodiment to occur within step 215 or within step 225, in lieu of the method 300 of FIG. 3A performed during step 205 in step 203. In such embodiments, if the mean intensity of the regions above the threshold T2 is low (e.g., less than a predetermined threshold, e.g., −150 HU in a CT image), the object is considered part-solid; otherwise it is considered solid.

Figure 4D:
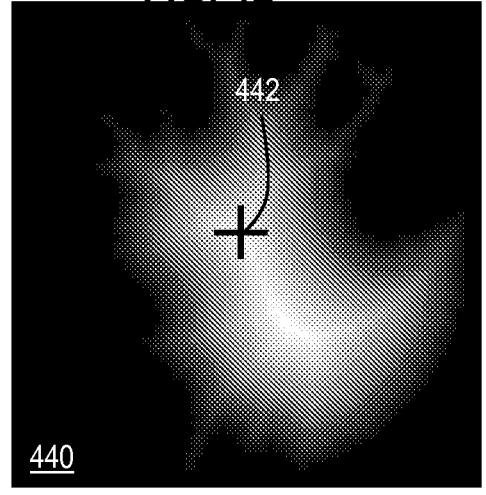
Figure 4E:
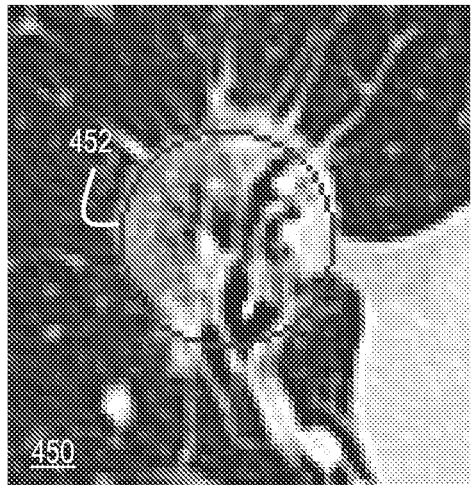

Step 339, to determine the distance of voxels within the target object to the closest edge of target object, is illustrated in FIG. 4D. FIG. 4D is an image that illustrates example distance values for each voxel within the subset of voxels 432 that indicate the target object, here are the lung lesion. Larger distances are lighter and the distance of zero is black. Step 341, to determine a center voxel at a local maximum distance equal to $\hat{R}$, is demonstrated by the center voxel 442; and, in FIG. 4E, by the circle 452 with radius $\hat{R}$ around center voxel 442. Starting with a voxel at the center of ROI 412 and walking a path to a neighbor with the largest distance, provided that distance is greater than the current voxel's own distance, the voxel with the local maximum distance to the edge is found. This voxel is considered the center voxel 442 for the object. The value of the distance at the center voxel 442 is the center distance $\hat{R}$. FIG. 4E is an image 450 that shows image data with the circle 452 representing the size and location of the target object, here the lung lesion. The watershed transform with markers, is initialized with the help of this circle 452 and the center voxel 442.

Step 343 is performed to select an interior marker for the watershed transform, and step 345 is performed to select and exterior marker. In an illustrated embodiment, the interior marker was chosen as a circle, centered at O, with a radius of a fraction (0.1 to 0.9, preferably 0.5) of $\hat{R}$. The ROI was applied to each slice of the VOI; voxels outside the ROI were considered exterior markers. Regions of typical background amplitude are also exterior markers. In other embodiments, to handle calcified lesions, the outer marker is adjusted so that it does not contain bright objects connected to the center of the ROI. It is anticipated that a similar rule would be useful for segmenting other objects as well.

Figure 4F:
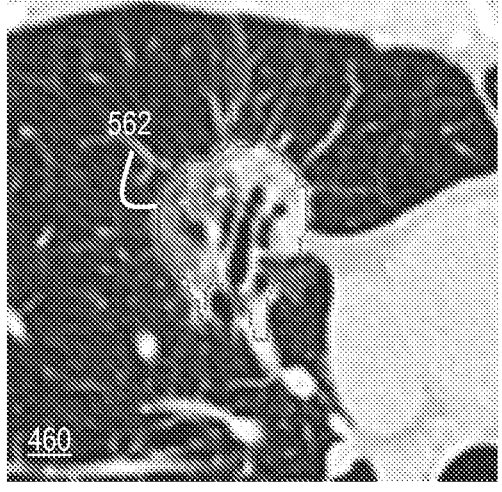

The results of the subsequent watershed transform is depicted in FIG. 4F. FIG. 4F is an image 460 on a slice close to the slice of image 410 in the image data. The watershed line 462 has more closely followed the boundary of the lung lesion in this slice of the image data. This watershed boundary, however, is rather irregular and appears to respond to the presence of adjacent vessels.

Figure 4G:
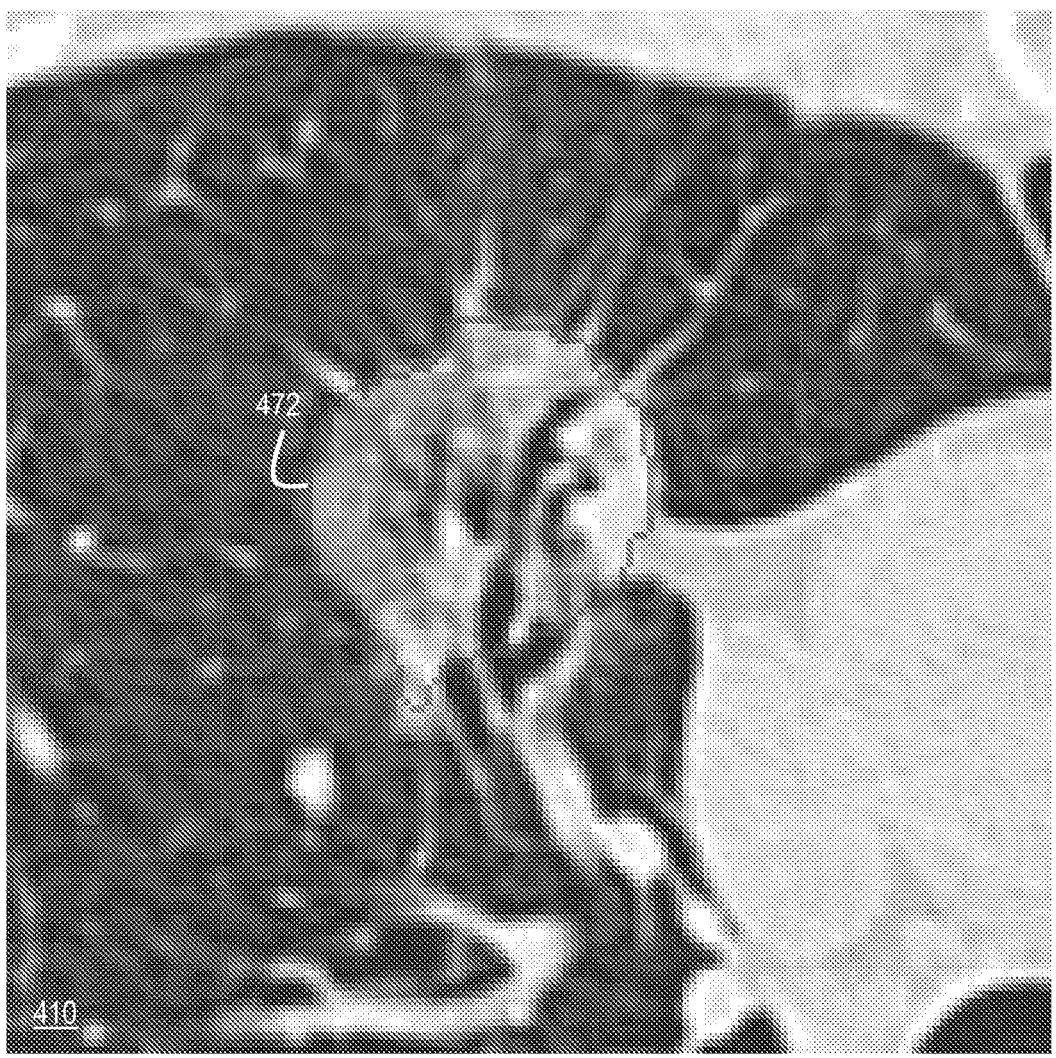

In step 241, the initial boundary 462, produced by the watershed transform, is refined using active contouring. FIG. 4G is an image that depicts the original image data from image 410 with refined boundary 472. The active contouring that produced boundary 472 was based on equation 9, with geometric, α and β terms, but without the topographical distance terms. Boundary 472 shows a smoothed boundary with vessels detached—a more satisfactory result. In other embodiments, other forms of the evolution equation are used.

On rare occasions when the density of the lung parenchyma has increased due to inflammation or other causes, some embodiments also include all the lung parenchyma. In such embodiments, the segmented GGO region(s) can be discarded and the active contour result can be directly used. Otherwise, the GGO region(s) can be combined with the active contour result, followed by morphological operations to detach thin structures.

Figure 6A:
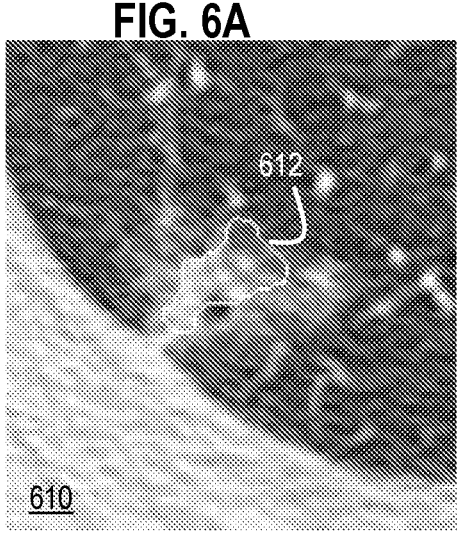
FIG. 6A through FIG. 6F are images that illustrate example results of segmenting part-solid lung lesions, according to an embodiment.
Figure 6B:
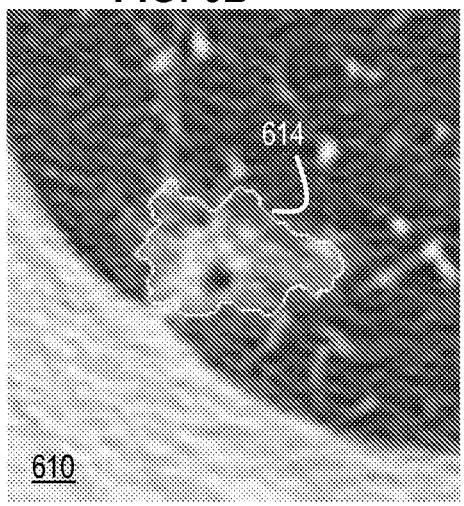
Figure 6C:
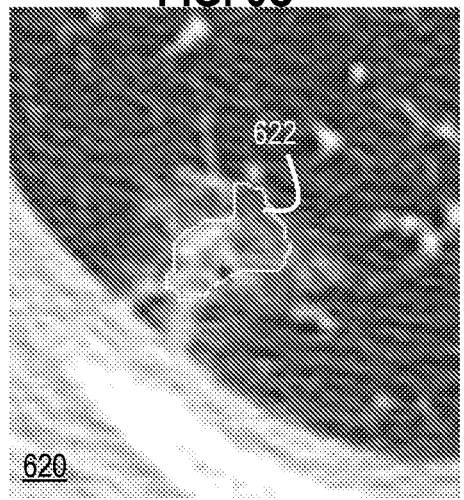
Figure 6D:
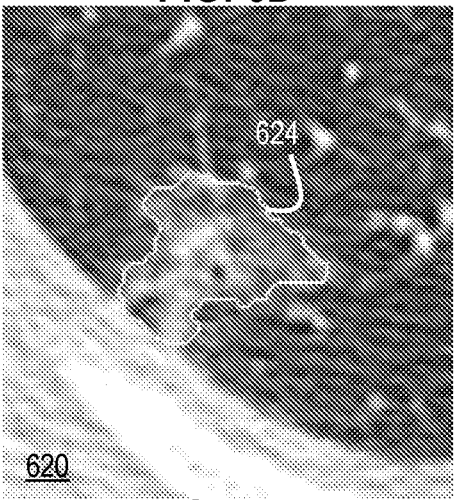
Figure 6E:
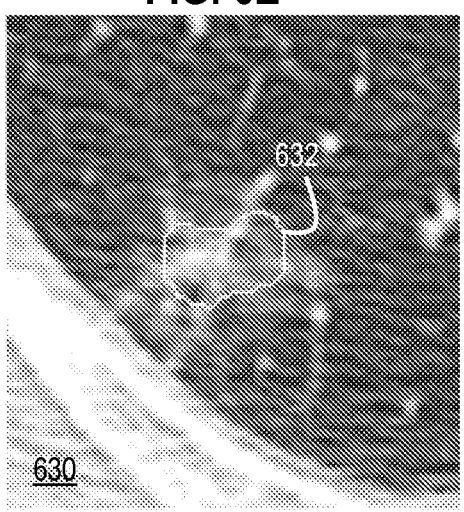
Figure 6F:
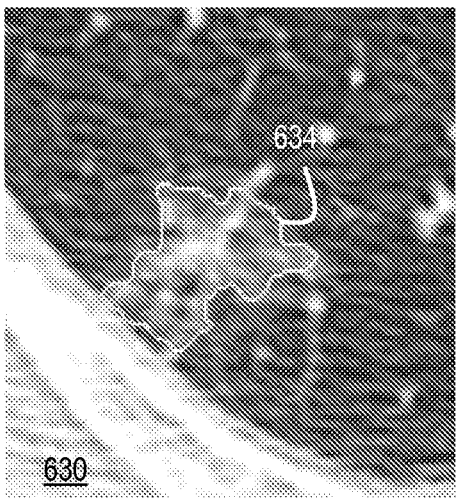

FIG. 6A through FIG. 6F are images that illustrate example results of segmenting part-solid lung lesions, according to an embodiment. The method described above with reference to step 255 of FIG. 2 is used in each case to expand a refined boundary to encompass GGO voxels for part solid lung lesions. FIG. 6A is an image that illustrates an example refined boundary 612 on an image 610 of a part solid lung lesion in a first slice, according to an embodiment. FIG. 6B is an image that illustrates an example expanded boundary 614 on the same image 610. The expanded boundary 614 successfully incorporates GGO voxels surrounding the refined boundary 612 for the part solid lung lesion. Similar results are obtained for other slices. For example, in a second slice. FIG. 6C depicts an example refined boundary 622 on an image 620; while, FIG. 6D depicts an expanded boundary 624 on image 620 that successfully incorporates GGO voxels. In the third slice, FIG. 6D depicts an example refined boundary 632 on image 630; while, FIG. 6F depicts an expanded boundary 634 on image 630 that successfully incorporates GGO voxels.

9. Mapping 3-D to 2-D Using Adjacent Rays

Some anatomical objects that that have roughly homogeneous intensity and are compact or roughly spherical in shape can be segmented very expeditiously using some alternative steps for method 200. In some embodiments, the object is an object within which there is a convenient reference point such that any line segment connecting the reference point with any other points in the object is also in the object. In various embodiments, the reference point is the center of an ROI, or is the center voxel determined from a distance transform after thresholding the object in the ROI/VOI, as described above, e.g., with reference to center voxel 442 in FIG. 4D. Thus, a center of a region of interest is determined in the image data.

In various embodiments, the reference slice is selected, for example, to be one that has the largest area of the target object, or a slice close to the center of the target object. In some embodiments, during step 221, the ROI is extended to 3D as follows. A 2D ROI on one slice is extended in a direction perpendicular to the slice to generate a cylindrical volume of interest (VOI). The amplitudes of voxels in the axially arranged cross sectional images in the VOI are converted to a radial or spherical amplitude distribution, from which the boundary of the 3D object can be determined in the full image data.

For example, from a point in the ROI on the reference image, e.g., the center point of an elliptical ROI, or another point in other images encompassed in the VOI, a number of radially distributed line segments (referred to as rays) are generated, such that the rays pass through the vertices of a subdivided unit sphere centered at the center point. Thus, a plurality of rays is determined, originating at the center in a corresponding plurality of directions. Furthermore, a plurality of adjacent rays is determined for each ray, based on their proximity on the surface of the unit sphere. The length 1 of each ray is selected to be sufficiently long to cover the target object, for example, by being sufficiently long to cover the ROI. For example, in embodiments in which the ROI is defined as an ellipse, the length of the rays is taken as twice the semi-major axis of the ROI. The amplitudes along each of the rays are sampled based on the original cross sectional slices of the image data. Thus, a series of amplitudes are determined at a corresponding plurality of distances from the center along each ray, based on an amplitude of a nearest voxel to each distance from center of the corresponding plurality of distances from the center.

Using the sampled intensities and the spatial arrangement of the rays, a path from the first ray to the last ray is determined that represents the boundary of the object. For example, in some embodiments, the path is determined by assigning a cost value to each point of an 2D image formed by plotting the sampled intensities against ordered positions of the rays for a potential move from the point of one ray to another point in the same ray or in a spatially adjacent ray, and finding the path having the lowest accumulative cost. Such a shortest path can be found by dynamic programming using the adjacency information in the spatial arrangement of the rays. This path obtained from 2D is then converted back into positions in 3D that delineate the boundary of the object of interest. Thus, a first boundary is determined based on a path of minimum cost to connect one position on each ray to one position on each of a plurality of adjacent rays.

In some embodiments, the segmentation result obtained from above is further refined by active contouring, as described above, or morphological operations, as described above, or some combination. Thus, in some embodiments, the method includes determining, on a processor, a refined boundary based on performing active contouring of the first boundary. In some embodiments, active contouring described above is further modified to take advantage of characteristics along the rays.

In various embodiments, the rays are generated to substantively evenly cover all the solid angles within the sphere. For example, in some embodiments, the rays are generated using sphere subdivision that approximates the sphere surface using triangle meshes of similar areas. In general, a surface of a solid object can be approximated by a triangle mesh. If the object is concave, that is, all the surfaces can be viewed from a single point within the object, then the triangle mesh can be determined by the distance and direction of each vertex of the mesh to that internal point. By shrinking (or extending) the distances to unit length, the triangle mesh is projected to a polyhedron inscribed in a unit sphere. The more number of faces the mesh has, the closer the deformed triangle mesh approximate the surface of the sphere.

Figure 7A:
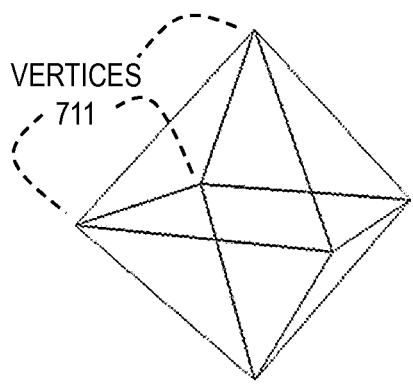
FIG. 7A, FIG. 7C and FIG. 7E are block diagrams that illustrate example vertices on a sphere that is divided into increasing numbers of triangular facets, respectively, and corresponding rays in FIG. 7B, FIG. 7D and FIG. 7F, respectively, according to an embodiment.
Figure 7B:
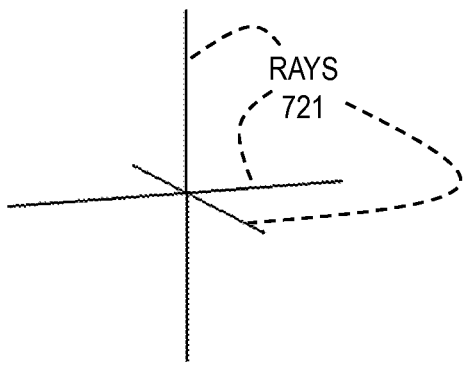
Figure 7C:
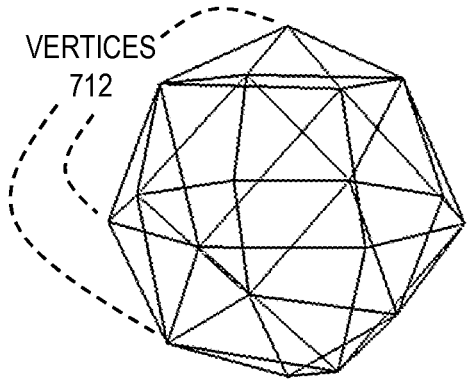
Figure 7D:
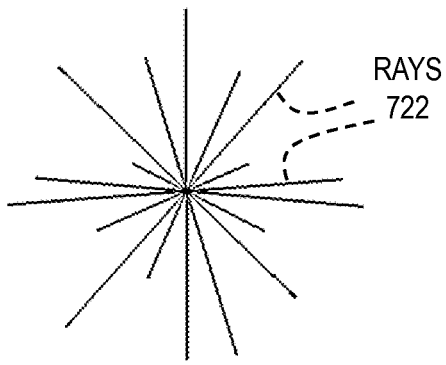
Figure 7E:
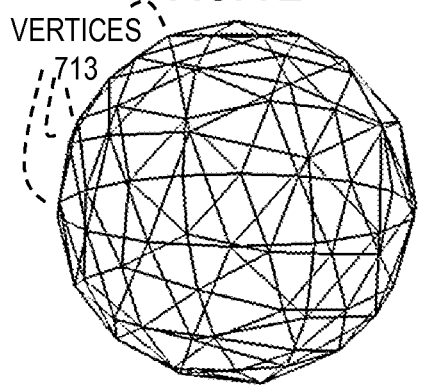
Figure 7F:
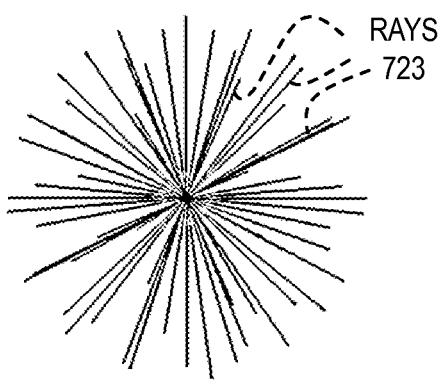

FIG. 7A, FIG. 7C and FIG. 7E are block diagrams that illustrate example vertices on a sphere that is divided into increasing numbers of triangular facets, respectively, and corresponding rays in FIG. 7B, FIG. 7D and FIG. 7F, respectively, according to an embodiment. FIG. 7A through FIG. 7F illustrate the approximation of a sphere by subdividing an octahedron. Starting from an octahedron (or any regular bi-pyramid), the subdivision can divide each triangle face into smaller ones. For convenience of reference, the sphere is described using geographical terms for the Earth. Note that the "north pole" and "south pole" of the sphere herein represent two arbitrary points that are radially opposed in the sphere. Taking an octahedron as an example, depicted in FIG. 7A, an octahedron has four vertices 711 on the equator and one vertex 711 on each of the north pole and south pole. The corresponding rays 721 are depicted in FIG. 7B. An n-level subdivision divides each edge on the equator into n edges by adding n−1 vertices, and adds vertices along n−1 latitudes. FIG. 7C depicts vertices 712 after a level 2 subdivision; and, FIG. 7D depicts the corresponding rays 722. FIG. 7E depicts vertices 713 after several further levels of subdivision; and, FIG. 7F depicts the corresponding rays 723. The rays 723 well approximate the unit sphere with vertices 713.

Vertices headed at the same level have the same latitude, which makes it easier to determine if a voxel is inside a mesh or not. A level n vertex V, the center of sphere O, and the north pole P form an angle (elevation) $\theta_n = \angle VOP$.

Since the southern hemisphere is symmetrical to the northern hemisphere, only the north hemisphere is described herein. Let the north pole be level 0, and the equator be level N. There are 4 points on the first level in the case of an octahedron (the number depends on the original bi-pyramid), forming 4 triangles with the north pole, and 4n points on the n-th level, forming 8n−4 triangles with points on level n−1. There are $4N^2$ triangle faces on the northern hemisphere, covering an area of $2\pi R^2$, where R is the radius of the sphere. To approximately cover the sphere with triangles of similar areas, each triangle can cover $\pi R^2/2N^2$, and the elevation of each level can be selected as given by Equation 12.

$$\theta_n = \arccos\left(1 - \frac{n^2}{N^2}\right). \quad (12)$$

The resulting angles are close to being evenly distributed. The degree of subdivision is selected according to the size of the object or the accuracy desired. A larger N allows a finer subdivision of the sphere, which can improve the segmentation accuracy (while decreasing the computational efficiency). Alternatively, the elevation angles can be evenly divided, which results in tetrahedrons of slightly larger solid angles close to the poles than the solid angles close to the equator. Thus, the plurality of rays intersect a sphere at a corresponding number of vertices that are similarly spaced from each other.

Adjacency can be captured by arranging the vertices in order with the closest vertices, closest in order. For example, the vertices of the above triangle mesh are arranged in order from north pole to south pole, and from west to east. FIG. 8 is a block diagram that illustrates adjacency of example vertices 712 on a sphere, and corresponding rays 722, according to an embodiment. Vertices 712 are indexed nodes and adjacency relationships 822 are edges that connect nodes. The vertices are indexed in order so that vertices that are adjacent in the order are also adjacent on the unit sphere. That is, successive rays are in order such that if a first ray is adjacent to a second ray in the order, then the second ray is among the plurality of adjacent rays for the first ray. For example, vertex 8 is adjacent to both 7 and 9; and, in fact, is adjacent to six vertices that are, counterclockwise from the top, numbered 2, 7, 17, 18, 19 and 9.

FIG. 8 shows the arrangement of part of the northern hemisphere for FIG. 7C by cutting along an "international dateline," where the zero vertex is the north pole and vertices 0, 4, 12, 24 are along the international dateline. The predecessors of a vertex can be viewed as the vertices that directly connect with the vertex by an edge 822 and have smaller vertex indices. The predecessor with the largest index is the vertex's immediate predecessor. For example, the predecessors of vertex 14 are vertex 5, 6, 13, and vertex 13 is the immediate predecessor. In FIG. 8, vertex i-1 is the immediate predecessor of vertex i for i>=1. The successors of a vertex can be defined in a similar way. The rays can be ordered by the vertices they pass through. As such, the adjacency information of these rays can also be readily obtained from the vertices the rays pass through. For example, Ray #2 (the ray that passes vertex 2) is spatially adjacent to Rays #0, #1, #3, #7, #8, and #9. Ray #2 is the immediate successor ray of Ray #1, and is the immediate predecessor ray of Ray #3. In general, the plurality of rays are ordered from a first ray at a first pole of the sphere to a not previously ordered adjacent ray in one direction along the same latitude line, if any, and, if not, to an adjacent ray on a next latitude.

Alternative ways to subdivide a sphere can also be used to generate a distribution of vertices that are substantially evenly distributed on the surface of the sphere. For example, if the number of vertices is given, the positions of the vertices can be mathematically derived such that they are substantially evenly distributed on the surface of the sphere. In alternative embodiments, a number of identical "point charges" (according to the desired number of vertices) are first placed on the surface of the sphere, and these point charges are allowed to move along the spherical surface to achieve an equilibrium due to the repulsive forces among them. The positions of these point charges at the equilibrium are obtained by computer simulation, and are considered the positions of the vertices for the purpose of ray generation, as described above. The predecessor vertices (or rays) or successor vertices (or rays) of a vertex (or ray) are determined, in these embodiments, based on the distances between the vertex and the other vertices along the spherical surface.

In some embodiments, the rays with the re-sampled amplitudes are arranged in the order defined above to form a 2D image. That is, a two dimensional field of amplitudes is determined on a first dimension that represents distance along a ray from the center and a second dimension that indicates successive rays in order, as defined above.

A path is determined in the 2D image to represent the boundary the target object. Such boundary is based on the large amplitude gradients near the boundary as opposed to the generally homogenous amplitudes along a ray from the center to the boundary.

In some embodiments, the path is found by assigning a cost value to each point of the 2D image for a potential move from the point of one ray to another point in the same ray or in a spatially adjacent ray (not necessarily the immediate predecessor ray or the immediate successor ray). The path having the lowest accumulative cost represents the object boundary. Such a lowest-cost path can be determined efficiently by dynamic programming using the adjacency information in the spatial arrangement of the rays, as further described below.

10. Dynamic Contouring Using Homogeneity or Discontinuity

In one embodiment, the cost function for each point in the 2D image includes a gradient cost, a homogeneity cost, and a discontinuity cost. In other embodiments, more or fewer costs are included. The gradient cost $C_g$ at a point (x,y) is defined such that a greater gradient has a smaller gradient cost. For example, $C_g$ is defined by Equation 13.

$$C_g(x, y) = 1 - \frac{g_{clamp}(x, y)}{\max(g_{clamp}(x, y))} \quad (13)$$

Where $g_{clamp}(x, y) = \text{gradient}(x, y) \quad \text{if gradient}(x, y) < C_0$
$\qquad\qquad = C_0 \qquad\qquad\qquad \text{if gradient}(x, y) \geq C_0$ The gradient is clamped in a maximum value of $C_0$ in the above equation. In equation 13, a voxel with a strong gradient has a gradient cost close to 0, and a voxel with a weak gradient has a gradient cost close to 1. Thus, determining the path of minimum cost further comprises minimizing a cost function that comprises a gradient cost; and, the gradient cost decreases with increased radial gradient at a candidate point along a ray. Choosing $C_0$ to be 50 is based on the observation that a gradient strength of 50 is strong enough. In other embodiments, a maximum gradient different from 50 is used. In some embodiments, no clamping is used.

The homogeneity cost at a point (x,y) in the 2D image reflects amplitude homogeneity of the ray passing the point. For example, in some embodiments, the homogeneity cost is defined as the weighted standard deviation of amplitude along the vertical line (or column, corresponding to points along a ray) x from the bottom point (x,0) to (x,y). In some embodiments, the points closer to (x,y) are weighted more. For example, in some embodiments, the weight of (x,0) is set to 1, and the weight of (x,y−j) is set to $\gamma^j$ where $\gamma \leq 1$. A typical value for $\gamma$ is selected in a range from about 0.2 to about 1, and is preferably selected to be 0.9. This weighting scheme makes amplitude variation at a greater distance from the boundary less significant, which can assist in the segmentation of lymph nodes with central necrosis. The weighted standard deviation of intensities $x_0, x_1, \ldots, x_N$ with weight $w_0, w_1, \ldots, w_N$ is then defined by Equation 14.

$$\sigma = \sqrt{\sum_{i=0}^{N} p_i(x_i - \mu)^2} \quad (14)$$

where $$p_i = w_i / \sum_{k=0}^{N} w_k \text{ and } \mu = \sum_{i=0}^{N} p_i x_i.$$

In some embodiments, the homogeneity cost is defined as a function of the weighted standard deviation of the point (x,y) relative to the standard deviation of a selected area on the reference slice. In various embodiments, the selected area is a window ranging in size from about 3×3 voxels to about 15×15 voxels For example, in some embodiments, a 7×7 window is taken from the center (near the origin of the rays) and the standard deviation $\sigma_0$ of the voxel amplitude inside the window is used to estimate the standard deviation of the target object (such as a lymph node). The standard deviations of the closest n voxels (n=5 in one test, and is selected in a range from about 3 to about 10 in other embodiments) from the center of the ROI are set to no less than $\sigma_0$. The homogeneity cost is then defined by equation 15:

$$Ch(x, y) = \max(1, \sigma(x,y)/\sigma_0) \text{ if } y < n \quad (15)$$
$$= \sigma(x,y)/\sigma_0 \quad \text{otherwise}$$

Thus, in some embodiments, determining the path of minimum cost further comprises minimizing a cost function that comprises a homogeneity cost. The homogeneity cost increases with deviations in the amplitude along at least a portion of the ray between the candidate point and the center. In the illustrated embodiment, the chain 80 cost is used in step 233 to determine the initial boundary surface.

In some embodiments, a discontinuity cost is also assigned for (x,y) as the boundary points on adjacent rays desirably have similar lengths from the center. The difference in y-values for two adjacent rays can be punished by the discontinuity cost. The larger the difference, the higher the punishment. For example, a quadratic function of the difference is used in some embodiments. Considering that a larger target object allows for larger deviations, the discontinuity cost is defined, in some embodiments, by equation 16.

$$C_d(y, y_{pred}) = \frac{(y - y_{pred})^2}{y} \quad (16)$$

Thus, in some embodiments, determining the path of minimum cost further comprises minimizing a cost function that comprises a discontinuity cost. The discontinuity cost increase with increased difference between a first distance from the center to a first candidate point on a first ray and a second distance from the center to a second candidate point on an adjacent ray.

In some embodiments, the cost for the first column is the weighted sum of the gradient cost and homogeneity cost, namely, $C_{accum}(0, y) = C_g(0, y) + \alpha C_h(0, y)$, where a is selected in a range from about 0 to about 50. In an illustrated embodiment, the predecessor of (0,y) is set to (0,y) itself. The accumulated cost of point (x,y) for x>0 is calculated recursively using at each step equation 17.

$$C_{accum}(x, y) = C_g(x, y) + \alpha C_h(x, y) + \quad (17)$$
$$\frac{1}{n_{pred}} \left( \sum_{pred} \min_{-s \leq t \leq s} \{C_{accum}(pred, y+t) + \beta C_d(y, y+t)\} \right)$$

where $\alpha$, $\beta$, and s are preselected constants, ranging from about 0 to about 50. In some embodiments $\alpha=1$, $\beta=1$ and s=4. Ray pred is a predecessor of ray x, and $n_{pred}$ is the number of predecessors of ray x. The minimum is taken from points that are from (pred, y−s) to (pred, y+s). The formula favors points on a boundary having similar distances to the center as their predecessors. The parent of (x,y) is set to be the point along its immediate predecessor ray such that the above curly bracket part takes minimum value.

The accumulation matrix $C_{accum}(x,y)$ is solved efficiently by dynamic programming. The minimum value along the last column corresponds to the minimum cost from any north pole point to a corresponding south pole point, and the 2D boundary can be traced back by following the parent point of the point with minimum cost.

When calculating the accumulation matrix for one column of the 2D image (x,y∈0, 1, i.e., the intensity along one ray), the dynamic programming can use only the information from its predecessors (or alternatively, use only the information only from its successors). Additionally, upon completion of a dynamic programming procedure using only the predecessor information, a second dynamic programming procedure can be carried out using the accumulated cost along the last column as the initial cost. Thus, determining the path of minimum cost further comprises determining the path of minimum cost in the two dimensional field.

Determining the path of minimum cost further comprises transforming the path of minimum cost in the two dimensional field to a boundary of voxels in the image data. The 2D segmentation result above can easily be converted back 3D. Each triangle on the mesh and the center forms a tetrahedron. For a give voxel, its elevation (latitude) determines which level it is in, and its longitude and elevation (latitude) determine which tetrahedron the ray passes through. The length of the line segment from the center to the voxel is used to ascertain whether the voxel is inside or outside the triangle mesh, i.e. inside or outside the target object. In this way, during step 225, the initial boundary surface in three dimensions is determined.

11. Active Contouring Using Hybrid Global and Local Regions

In the illustrated embodiment, the initial boundary of the object determined according to the procedure above is further refined by active contouring to improve the result, such as increasing the smoothness of the surface or removing incorrectly included object portions. To this end, the conventional Chan-Vese active contour model, localized region-based active contours, or other 3D active contour methods can be used in various embodiments. Particularly, the amplitudes of the object can be modeled as constant and the amplitudes of the object on the boundary are locally different from those of the background; therefore, the contour can evolve by minimizing an energy functional as given by Equation 18.

$$E(\varphi(x)) = \lambda \int_\Omega |\nabla H(\varphi(x))| dx + \int_\Omega (1 - H(\varphi(x)))(u(x) - c)^2 dx + \int_\Omega \delta(\varphi(x)) \int B(x,y) H(\varphi(y))(u(y) - v(x))^2 dy dx \quad (18)$$

where $\varphi(x)$ is a level set function that has negative values at points inside the boundary, positive values at points outside the boundary, and zero on the boundary; H is the Heaviside function; u(x) is the image amplitudes at point x; c is an average (or, in other embodiments, an other statistical metric, such as variance) of the amplitude of all voxels inside the boundary. B(x,y) is a non-negative function that takes small value or 0 when point x is far from point y, as in a local regional statistical term. Since $\delta(\varphi(x))$ is non-zero only when x is on the zero level set of the level set function, v(x) can be defined for the points on the zero level set of $\varphi$. v(x) is the weighted average amplitudes of voxels that are at the vicinity of voxel x and have a positive value. In this notation, a boldface x or y indicates a vector quantity.

Given $\varphi(x)$, to minimize the energy E, c and v(x) are determined as given by equation 19 and equation 20, respectively.

$$c = \frac{\int_\Omega u(x) H(\varphi(x)) dx}{\int_\Omega H(\varphi(x)) dx} \quad (19)$$

$$v(x) = \frac{\int_\Omega B(x, y) H(\varphi(y)) u(y) dy}{\int_\Omega B(x, y) H(\varphi(y)) dy}, \quad (20)$$

where $\varphi(x) = 0$

Evolution of the contour is achieved by moving the contour to a local minimum of the energy E, e.g., by using the following gradient descent flow given by equation 21.

$$\varphi_t(x) = \delta(\varphi(x))(u(x) - c)^2 - \quad (21)$$

$$\delta(\varphi(x)) \int B(x, y) \delta(\varphi(y))(u(y) - v(x))^2 dy + \lambda \delta(\varphi(x)) div\left(\frac{\nabla \varphi(x)}{|\nabla \phi(x)|}\right)$$

The calculation of the gradient descent flow can be interleaved with that of c, v(x). The use of the function B to limit the effect of statistics outside the boundary to local effects along with the first term that includes deviations of all voxels inside the boundary from the average amplitude of all voxels inside the boundary is a novel hybrid approach. Thus, by virtue of equation 21, performing active contouring of the first boundary comprises using an evolution equation that includes a first term and a second term. The first term indicates deviations in amplitude for all voxels inside the boundary from an average amplitude of all voxels inside the boundary. The second term that indicates deviations in amplitude for local voxels outside the boundary from an average amplitude of the local voxels outside the boundary. When the function B excludes more than half of the voxels outside the boundary, which is advantageous for computational efficiency, the local voxels outside the boundary exclude a larger number of voxels outside the boundary.

12. Example Embodiments

Figure 9:
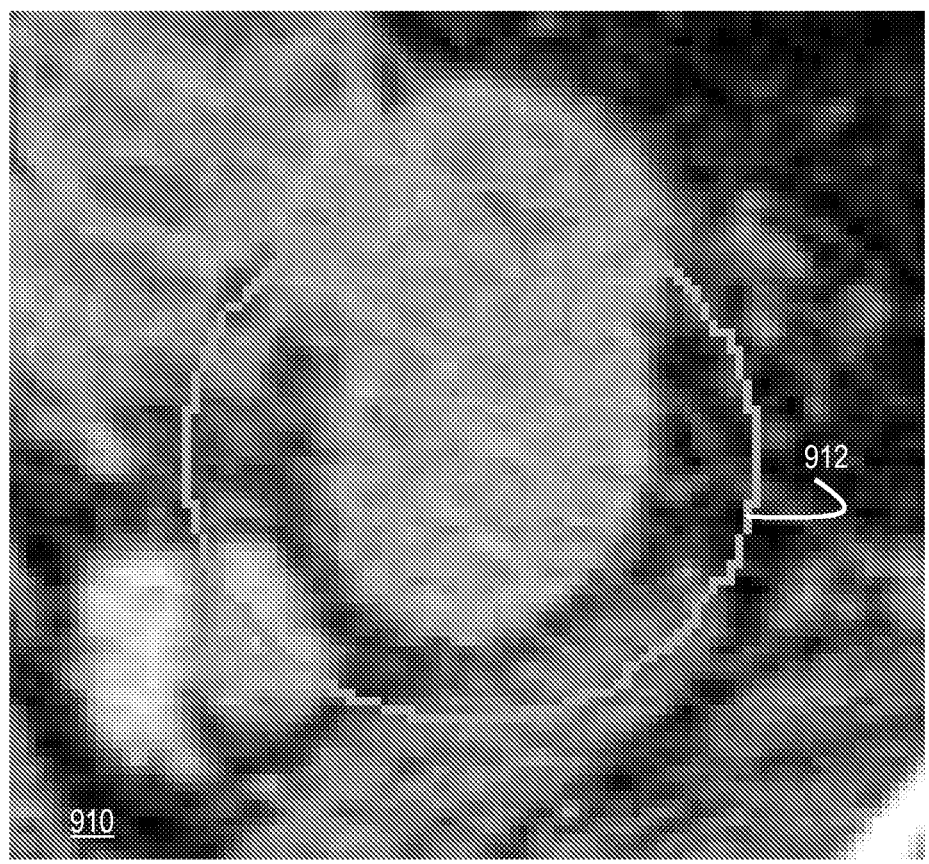
FIG. 9 is an image that illustrates example lymph node image data and region of interest on a reference slice, according to an embodiment.
Figure 11A:
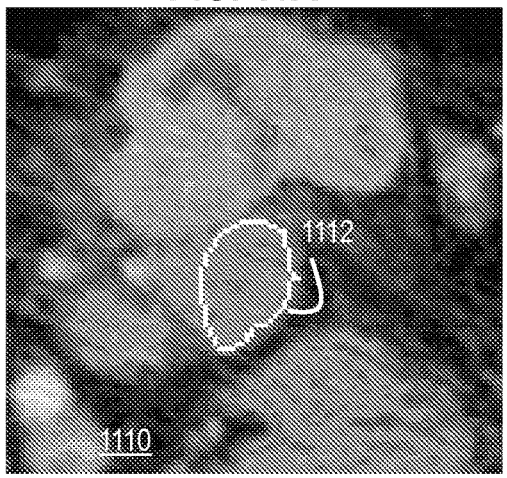
FIG. 11A through FIG. 11F are images that illustrate example results on six slices, respectively, of segmenting a lymph node in image data using rays, according to an embodiment.
Figure 11B:
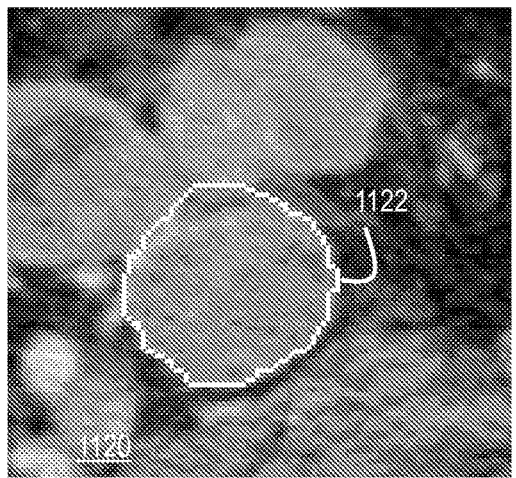
Figure 11C:
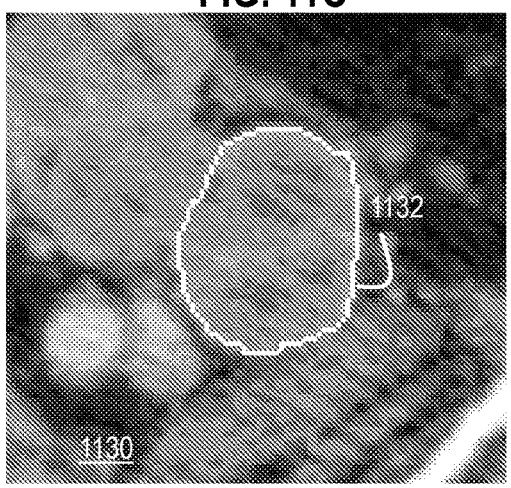
Figure 11D:
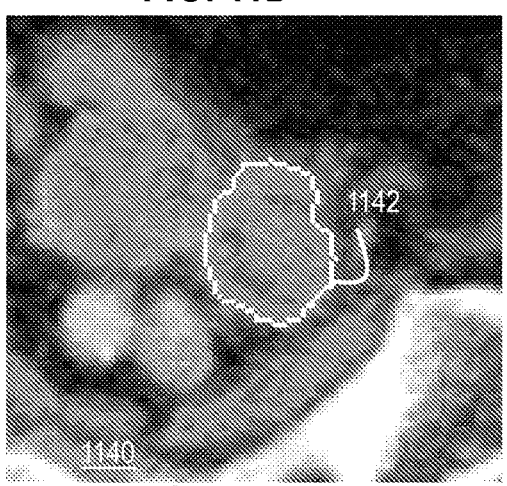
Figure 11E:
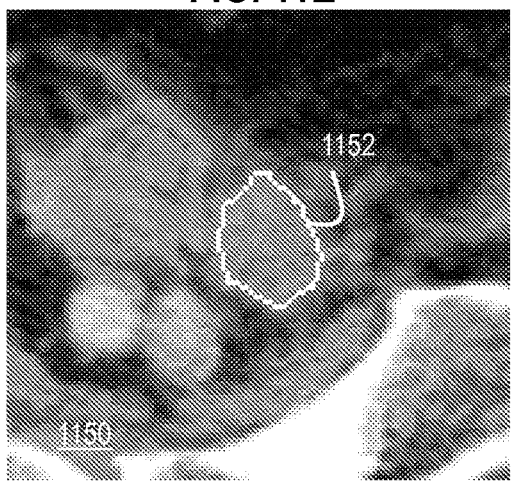
Figure 11F:
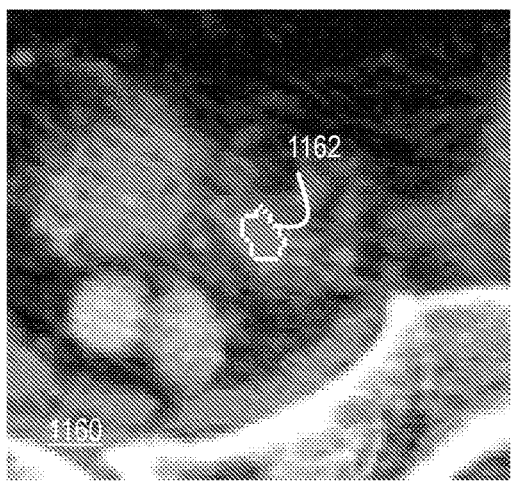

The use of rays to determine the boundary is demonstrated for lymph nodes. FIG. 9 is an image that illustrates example lymph node CT image data and region of interest 912 on a reference slice 910, according to an embodiment. An elliptical ROI is selected on a reference image, and a VOI is generated based on the ROI. In the illustrated embodiment, the VOI is sampled to convert the densities of the cross sectional images to densities along 698 rays generated using the sphere subdivision described above starting with an octahedron (N=13).

The rays with the sampled intensities are then arranged in the order defined above to form a 2D image, as shown in FIG. 10A. FIG. 10A is a two dimensional image that illustrates example three-dimensional image data mapped to two dimensions along a set of ordered rays, according to an embodiment. The horizontal axis 1002 indicates ray index number; and, the vertical axis 1004 indicates distance along a ray from the center. The grayscale 1010 at each position in FIG. 10A is proportional to the density on that ray at that distance from the center.

FIG. 10B is a two dimensional image that illustrates example three-dimensional image data mapped to two dimensions along a set of ordered rays with a boundary determined, according to an embodiment. The horizontal axis 1002, the vertical axis 1004 and the grayscale values 1010 are as described above. The boundary determined by dynamic programming with a homogeneity cost term, as well as a gradient cost term and a discontinuity cost term, is shown by trace 1012. This trace indicates the boundary of the lymph node in this image data. In various embodiments, this trace is mapped to three dimensions as described above, to provide an initial boundary for the lymph node.

FIG. 11A through FIG. 11F are images that illustrate example results on six slices, given by images 1110, 1120, 1130, 1140, 1150, and 1160, respectively, of segmenting a lymph node in image data using rays, according to an embodiment. White contour lines 1112, 1122, 1132, 1142, 1152, and 1162, respectively, indicate the boundaries determined for the lymph node on the selected slices. These boundaries successfully segmented for lymph nodes in the slices even in the presence of multiple features of similar density.

On occasions, thin structures that are not part of the lymph node are included in the segmentation result. Such a result can be further refined by morphological operations, in which thin objects can be detached by an eroding operation. The largest component can then be dilated, and "ANDed" with the active contour result to recover the detail of the boundary.

13. Hardware Overview

Figure 12:
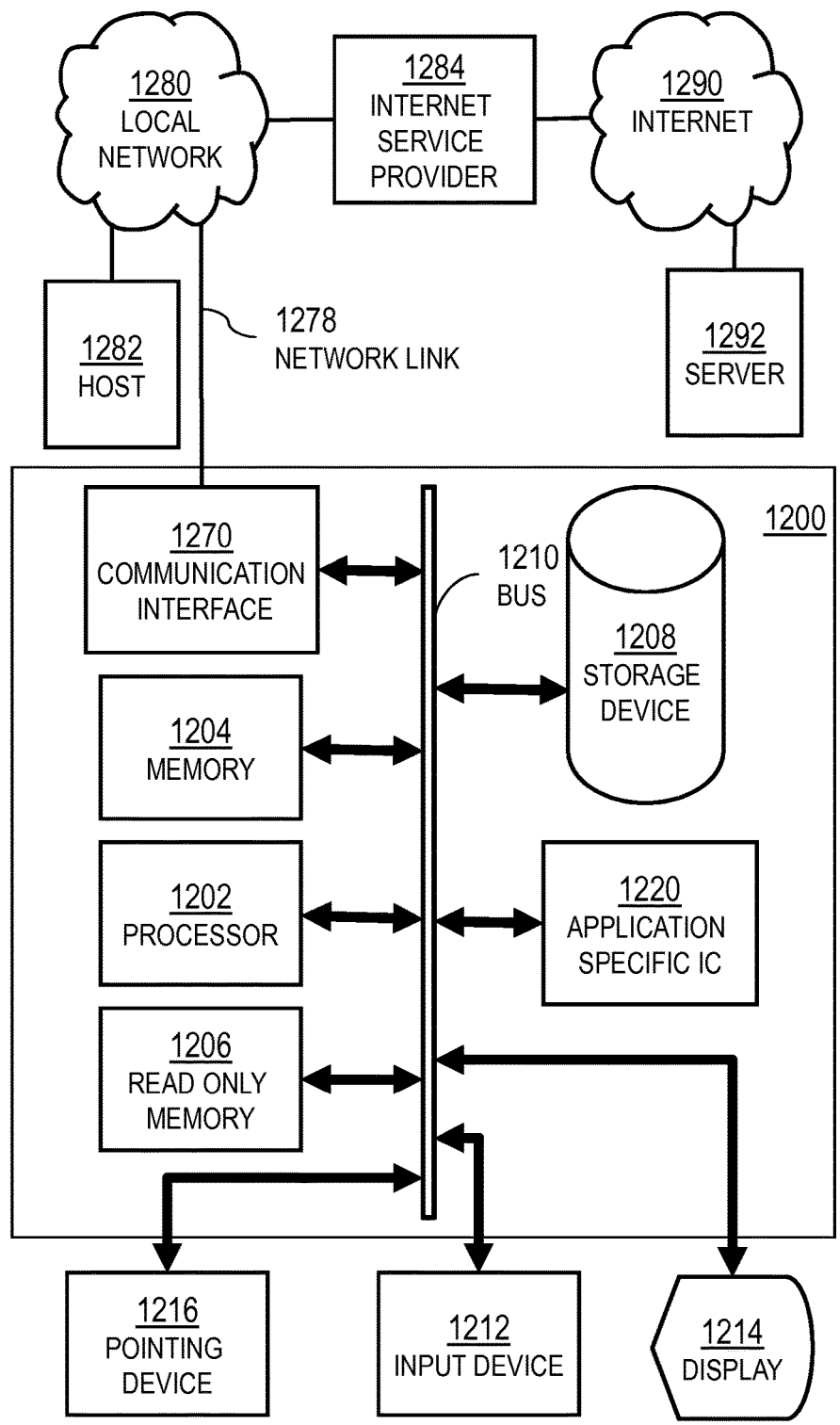
FIG. 12 is a block diagram that illustrates a computer system upon which an embodiment of the invention may be implemented.

FIG. 12 is a block diagram that illustrates a computer system 1200 upon which an embodiment of the invention may be implemented. Computer system 1200 includes a communication mechanism such as a bus 1210 for passing information between other internal and external components of the computer system 1200. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1200, or a portion thereof, constitutes a means for performing one or more steps of one or more methods described herein.

A sequence of binary digits constitutes digital data that is used to represent a number or code for a character. A bus 1210 includes many parallel conductors of information so that information is transferred quickly among devices coupled to the bus 1210. One or more processors 1202 for processing information are coupled with the bus 1210. A processor 1202 performs a set of operations on information. The set of operations include bringing information in from the bus 1210 and placing information on the bus 1210. The set of operations also typically include comparing two or more units of information, shifting positions of units of information, and combining two or more units of information, such as by addition or multiplication. A sequence of operations to be executed by the processor 1202 constitute computer instructions.

Computer system 1200 also includes a memory 1204 coupled to bus 1210. The memory 1204, such as a random access memory (RAM) or other dynamic storage device, stores information including computer instructions. Dynamic memory allows information stored therein to be changed by the computer system 1200. RAM allows a unit of information stored at a location called a memory address to be stored and retrieved independently of information at neighboring addresses. The memory 1204 is also used by the processor 1202 to store temporary values during execution of computer instructions. The computer system 1200 also includes a read only memory (ROM) 1206 or other static storage device coupled to the bus 1210 for storing static information, including instructions, that is not changed by the computer system 1200. Also coupled to bus 1210 is a non-volatile (persistent) storage device 1208, such as a magnetic disk or optical disk, for storing information, including instructions, that persists even when the computer system 1200 is turned off or otherwise loses power.

Information, including instructions, is provided to the bus 1210 for use by the processor from an external input device 1212, such as a keyboard containing alphanumeric keys operated by a human user, or a sensor. A sensor detects conditions in its vicinity and transforms those detections into signals compatible with the signals used to represent information in computer system 1200. Other external devices coupled to bus 1210, used primarily for interacting with humans, include a display device 1214, such as a cathode ray tube (CRT) or a liquid crystal display (LCD), for presenting images, and a pointing device 1216, such as a mouse or a trackball or cursor direction keys, for controlling a position of a small cursor image presented on the display 1214 and issuing commands associated with graphical elements presented on the display 1214.

In the illustrated embodiment, special purpose hardware, such as an application specific integrated circuit (IC) 1220, is coupled to bus 1210. The special purpose hardware is configured to perform operations not performed by processor 1202 quickly enough for special purposes. Examples of application specific ICs include graphics accelerator cards for generating images for display 1214, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1200 also includes one or more instances of a communications interface 1270 coupled to bus 1210. Communication interface 1270 provides a two-way communication coupling to a variety of external devices that operate with their own processors, such as printers, scanners and external disks. In general the coupling is with a network link 1278 that is connected to a local network 1280 to which a variety of external devices with their own processors are connected. For example, communication interface 1270 may be a parallel port or a serial port or a universal serial bus (USB) port on a personal computer. In some embodiments, communications interface 1270 is an integrated services digital network (ISDN) card or a digital subscriber line (DSL) card or a telephone modem that provides an information communication connection to a corresponding type of telephone line. In some embodiments, a communication interface 1270 is a cable modem that converts signals on bus 1210 into signals for a communication connection over a coaxial cable or into optical signals for a communication connection over a fiber optic cable. As another example, communications interface 1270 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1270 sends and receives electrical, acoustic or electromagnetic signals, including infrared and optical signals, that carry information streams, such as digital data.

The term computer-readable medium is used herein to refer to any medium that participates in providing information to processor 1202, including instructions for execution. Such a medium may take many forms, including, but not limited to, non-volatile media, volatile media and transmission media. Non-volatile media include, for example, optical or magnetic disks, such as storage device 1208. Volatile media include, for example, dynamic memory 1204. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1202, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1202, except for carrier waves and other signals.

Logic encoded in one or more tangible media includes one or both of processor instructions on a computer-readable storage media and special purpose hardware, such as ASIC 1220.

Network link 1278 typically provides information communication through one or more networks to other devices that use or process the information. For example, network link 1278 may provide a connection through local network 1280 to a host computer 1282 or to equipment 1284 operated by an Internet Service Provider (ISP). ISP equipment 1284 in turn provides data communication services through the public, world-wide packet-switching communication network of networks now commonly referred to as the Internet 1290. A computer called a server 1292 connected to the Internet provides a service in response to information received over the Internet. For example, server 1292 provides information representing video data for presentation at display 1214.

The invention is related to the use of computer system 1200 for implementing the techniques described herein. According to one embodiment of the invention, those techniques are performed by computer system 1200 in response to processor 1202 executing one or more sequences of one or more instructions contained in memory 1204. Such instructions, also called software and program code, may be read into memory 1204 from another computer-readable medium such as storage device 1208. Execution of the sequences of instructions contained in memory 1204 causes processor 1202 to perform the method steps described herein. In alternative embodiments, hardware, such as application specific integrated circuit 1220, may be used in place of or in combination with software to implement the invention. Thus, embodiments of the invention are not limited to any specific combination of hardware and software.

The signals transmitted over network link 1278 and other networks through communications interface 1270, carry information to and from computer system 1200. Computer system 1200 can send and receive information, including program code, through the networks 1280, 1290 among others, through network link 1278 and communications interface 1270. In an example using the Internet 1290, a server 1292 transmits program code for a particular application, requested by a message sent from computer 1200, through Internet 1290, ISP equipment 1284, local network 1280 and communications interface 1270. The received code may be executed by processor 1202 as it is received, or may be stored in storage device 1208 or other non-volatile storage for later execution, or both. In this manner, computer system 1200 may obtain application program code in the form of a signal on a carrier wave.

Various forms of computer readable media may be involved in carrying one or more sequence of instructions or data or both to processor 1202 for execution. For example, instructions and data may initially be carried on a magnetic disk of a remote computer such as host 1282. The remote computer loads the instructions and data into its dynamic memory and sends the instructions and data over a telephone line using a modem. A modem local to the computer system 1200 receives the instructions and data on a telephone line and uses an infra-red transmitter to convert the instructions and data to a signal on an infra-red carrier wave serving as the network link 1278. An infrared detector serving as communications interface 1270 receives the instructions and data carried in the infrared signal and places information representing the instructions and data onto bus 1210. Bus 1210 carries the information to memory 1204 from which processor 1202 retrieves and executes the instructions using some of the data sent with the instructions. The instructions and data received in memory 1204 may optionally be stored on storage device 1208, either before or after execution by the processor 1202.

Figure 13:
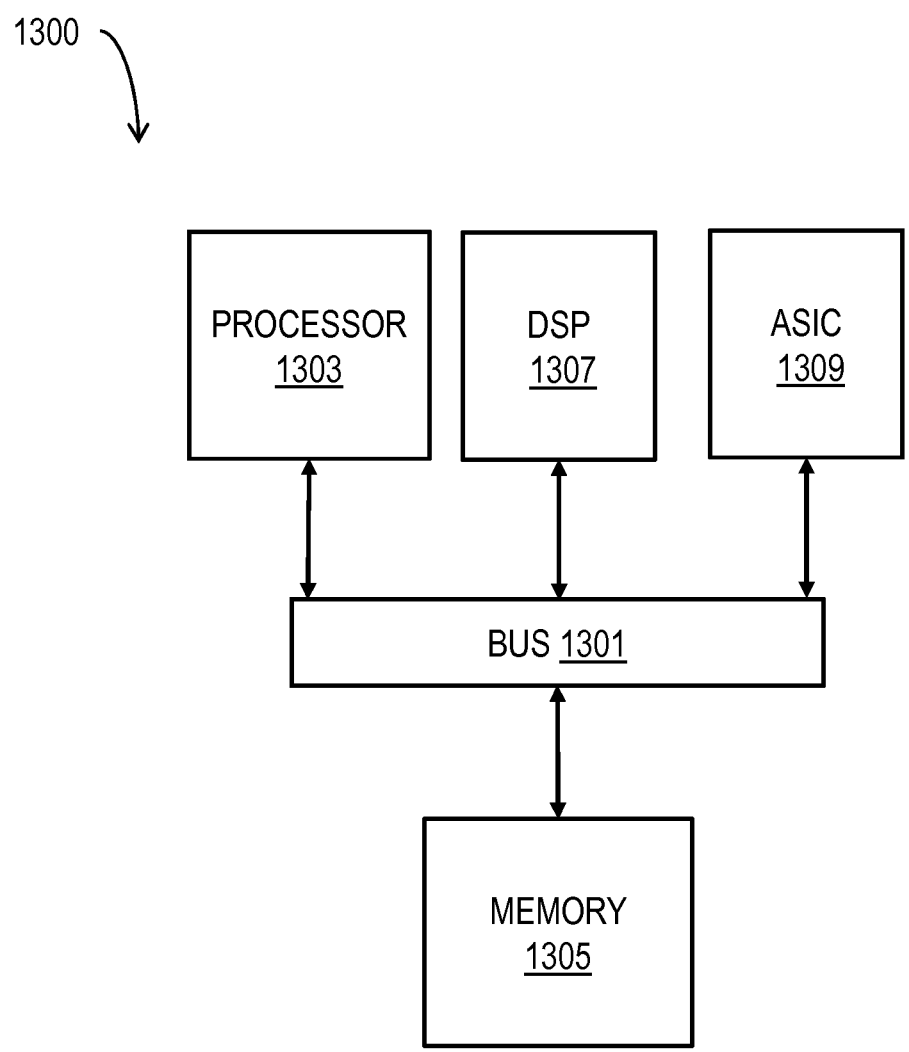
FIG. 13 illustrates a chip set upon which an embodiment of the invention may be implemented.

FIG. 13 illustrates a chip set 1300 upon which an embodiment of the invention may be implemented. Chip set 1300 is programmed to perform one or more steps of a method described herein and includes, for instance, the processor and memory components described with respect to FIG. 12 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1300, or a portion thereof, constitutes a means for performing one or more steps of a method described herein.

In one embodiment, the chip set 1300 includes a communication mechanism such as a bus 1301 for passing information among the components of the chip set 1300. A processor 1303 has connectivity to the bus 1301 to execute instructions and process information stored in, for example, a memory 1305. The processor 1303 may include one or more processing cores with each core configured to perform independently. A multi-core processor enables multiprocessing within a single physical package. Examples of a multi-core processor include two, four, eight, or greater numbers of processing cores. Alternatively or in addition, the processor 1303 may include one or more microprocessors configured in tandem via the bus 1301 to enable independent execution of instructions, pipelining, and multithreading. The processor 1303 may also be accompanied with one or more specialized components to perform certain processing functions and tasks such as one or more digital signal processors (DSP) 1307, or one or more application-specific integrated circuits (ASIC) 1309. A DSP 1307 typically is configured to process real-world signals (e.g., sound) in real time independently of the processor 1303. Similarly, an ASIC 1309 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1303 and accompanying components have connectivity to the memory 1305 via the bus 1301. The memory 1305 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1305 also stores the data associated with or generated by the execution of one or more steps of the methods described herein.

14. Extensions, Modifications and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

15. References

L. Vincent and P. Soille, "Watersheds in digital spaces: an efficient algorithm based on immersion simulations," *IEEE Transactions On Pattern Analysis And Machine Intelligence*, v. 13 (6), pp 583-598, June 1991.

Meyer, F. "Topographic distance and watershed lines." Signal Processing 38(1): 113-125, 1994.

What is claimed is:

1. A method comprising
obtaining, on a processor, image data that indicates amplitude values at each of a plurality of voxels for a particular measurement modality; determining, on a processor, an outer edge of a contiguous subset of voxels based on voxels that have an amplitude in a first amplitude range associated with a target object in image data of the particular measurement modality;
determining, on a processor, a center voxel, wherein a center distance from the center voxel to a closest voxel of the outer edge is greater than a distance from any neighbor of the center voxel to a corresponding closest voxel of the outer edge;
determining, on a processor, a location and size of the target object in the image data based on the center voxel and the center distance further comprising
determining, on a processor, a refined boundary by moving an initial boundary based on active contouring using as the initial boundary at least one of the center voxel and the center distance or a watershed boundary; and
presenting on a display device output image data based at least in part on the refined boundary,
wherein the active contouring of the initial boundary further comprises determining a
change in boundary position based, at least in part, on a potential well term independently weighted by a parameter a with value greater than 1;
the potential well term comprises a product of a gradient of an edge indicator function g and a gradient of a level set function Φ, and the edge indicator function g includes both a gradient edge detector and a Canny edge detector.

2. A method comprising:
obtaining, on a processor, image data that indicates amplitude values at each of a plurality of voxels for a particular measurement modality;
determining, on a processor, an outer edge of a contiguous subset of voxels based on voxels that have an amplitude in a first amplitude range associated with a target object in image data of the particular measurement modality;
determining, on a processor, a center voxel, wherein a center distance from the center voxel to a closest voxel of the outer edge is greater than a distance from any neighbor of the center voxel to a corresponding closest voxel of the outer edge;
determining, on a processor, a location and size of the target object in the image data based on the center voxel and the center distance further comprising:
determining, on a processor, based on a Markov model and on an amplitude range for background voxels and an amplitude range for part-solid voxels, whether a voxel outside and adjacent to a current boundary that is based on at least one of the center voxel and the center distance or a watershed boundary belongs to a background set or a first part-solid set;
determining, on a processor, whether the voxel belongs to a solid tissue set or a second part-solid set based on a Markov model and on an amplitude range for solid tissue voxels and the amplitude range for part-solid voxels; and
determining, on a processor, a refined boundary by moving the current boundary to encompass the voxel if the voxel belongs to the first part-solid set and to the second part-solid set; and
presenting on a display device output image data based at least in part on the location and size of the target object or the refined boundary,
wherein the amplitude range for part-solid voxels overlaps on one end the amplitude range for solid tissue voxels and overlaps on the opposite end the amplitude range for background voxels.

3. The method as recited in claim 2, wherein the background voxels represent lung parenchyma, the solid tissue voxels represent solid lung lesion tissue, and the part-solid voxels represent ground glass opacities (GGO) lung lesion tissue.

4. The method as recited in claim 2, further comprising, only determining whether the voxel belongs to the first part-solid set and determining whether the voxel belongs to the second part-solid set, if it is determined, on a processor, that the target object likely involves sufficient part-solid tissue.

5. The method as recited in claim 4, further comprising
determining, on a processor, a first set of contiguous voxels with amplitudes above a first threshold;
determining, on a processor, a first subset of the first set, wherein the first subset includes voxels with amplitudes above a second, larger threshold;
determining, on a processor, a ring of voxels in the first set and outside the first subset and adjacent to the first subset;
determining, on a processor, a second subset of the first set, wherein the second subset excludes the ring and excludes the first subset; and
determining, on a processor, that the target object likely involves sufficient part-solid tissue if a number of voxels in the second subset is greater than a number of voxels in the ring.

6. The method as recited in claim 4, determining that the target object likely involves sufficient part-solid tissue further comprising determining that an average amplitude inside the current boundary is below a particular value.

7. A method comprising:
obtaining, on a processor, image data that indicates amplitude values at each of a plurality of voxels for a particular measurement modality;
determining, on a processor, an outer edge of a contiguous subset of voxels based on voxels that have an amplitude in a first amplitude range associated with a target object in image data of the particular measurement modality;

determining, on a processor, for the target object a single center voxel inside the outer edge, wherein a center distance from the center voxel to a closest voxel of the outer edge is greater than a distance from any neighbor of the center voxel to a corresponding closest voxel of the outer edge;

determining, on a processor, a location and size of the target object in the image data based on the center voxel and the center distance further comprising:

generating, on a processor, a plurality of rays originating at the center voxel in a corresponding plurality of directions in three dimensions;

converting, on a processor, the plurality of rays in three dimensions to a plurality of adjacent rays in two dimensions;

generating, on a processor, a series of amplitudes at a corresponding plurality of distances from the center voxel along each ray of the plurality of rays, each amplitude along a ray of the plurality of rays based on an amplitude of a nearest voxel to each distance from the center voxel of the corresponding plurality of distances from the center voxel; and generating, on a processor, an initial boundary based on connecting a path of minimum cost from one position on each ray of the plurality of rays to one position on each of a plurality of adjacent rays; and presenting on a display device output image data based at least in part on the initial boundary.

8. The method as recited in claim 7, wherein determining the path of minimum cost further comprises minimizing a cost function that comprises a gradient cost and a homogeneity cost, wherein:

the gradient cost decreases with increasing radial gradient at a candidate point along the ray; and the homogeneity cost increases with deviations in the amplitude along the ray in at least a portion of the ray between the candidate point and the center voxel.

9. The method as recited in claim 7, wherein determining the path of minimum cost further comprises minimizing a cost function that comprises a discontinuity cost, wherein the discontinuity cost increases with increasing difference between a first distance from the center voxel to a first candidate point on a first ray and a second distance from the center voxel to a second candidate point on an adjacent ray.

10. The method as recited in claim 7, wherein determining the path of minimum cost further comprises:

determining a two dimensional field of amplitudes on a first dimension that represents distance along a ray from the center voxel and a second dimension that indicates successive rays in order such that if a first ray is adjacent to a second ray in the second dimension, then the second ray is among the plurality of adjacent rays for the first ray, determining the path of minimum cost in the two dimensional field; and transforming the path of minimum cost in the two dimensional field to a boundary of voxels in the image data.

11. The method as recited in claim 10, wherein the plurality of rays originating at the center voxel intersect a sphere at a corresponding number of vertices that are similarly spaced from each other.

12. The method as recited in claim 11, wherein the plurality of rays originating at the center voxel are ordered from a first ray at a first pole of the sphere to a not previously ordered adjacent ray in one direction along the same latitude line, if any, and if not, to an adjacent ray on a next latitude.

13. The method as recited in claim 10, wherein a first ray of the plurality of rays originating at the center voxel is adjacent to a plurality of other rays that intersect the sphere closest to the first ray.

14. The method as recited in claim 7, further comprising determining, on a processor, a refined boundary based on performing active contouring of the initial boundary.

15. The method as recited in claim 14, wherein performing active contouring of the first boundary comprises using an evolution equation that includes a first term that indicates deviations in amplitude for all voxels inside the boundary from an average amplitude of all voxels inside the boundary and a second term that indicates deviations in amplitude for local voxels outside the boundary from an average amplitude of the local voxels outside the boundary, wherein the local voxels outside the boundary exclude a larger number of voxels outside the boundary.

16. A non-transitory computer-readable medium carrying one or more sequences of instructions, wherein execution of the one or more sequences of instructions by one or more processors causes the one or more processors to perform the steps of:

obtaining image data that indicates amplitude values at each of a plurality of voxels for a particular measurement modality;

determining an outer edge of a contiguous subset of voxels based on voxels that have an amplitude in a first amplitude range associated with a target object in image data of the particular measurement modality;

determining a center voxel, wherein a center distance from the center voxel to a closest voxel of the outer edge is greater than a distance from any neighbor of the center voxel to a corresponding closest voxel of the outer edge;

determining a location and size of the target object in the image data based on the center voxel and the center distance further comprising determining based on a Markov model and on an amplitude range for background voxels and an amplitude range for part-solid voxels, whether a voxel outside and adjacent to a current boundary that is based on at least one of the center voxel and the center distance or a watershed boundary belongs to a background set or a first part-solid set;

determining whether the voxel belongs to a solid tissue set or a second part-solid set based on a Markov model and on an amplitude range for solid tissue voxels and the amplitude range for part-solid voxels; and determining a refined boundary by moving the current boundary to encompass the voxel if the voxel belongs to the first part-solid set and to the second part-solid set; and presenting on a display device output image data based at least in part on the location and size of the target object or the refined boundary, wherein the amplitude range for part-solid voxels overlaps on one end the amplitude range for solid tissue voxels and overlaps on the opposite end the amplitude range for background voxels.

17. A system comprising:
a display device;
at least one processor; and
at least one memory including one or more sequences of instructions, the at least one memory and the one or more sequences of instructions configured to, with the at least one processor, cause an apparatus to perform at least the following:
  obtain image data that indicates amplitude values at each of a plurality of voxels for a particular measurement modality;
  determine an outer edge of a contiguous subset of voxels based on voxels that have an amplitude in a first amplitude range associated with a target object in image data of the particular measurement modality;
  determine a center voxel, wherein a center distance from the center voxel to a closest voxel of the outer edge is greater than a distance from any neighbor of the center voxel to a corresponding closest voxel of the outer edge; and
  determine a location and size of the target object in the image data based on the center voxel and the center distance further comprising
    determine based on a Markov model and on an amplitude range for background voxels and an amplitude range for part-solid voxels, whether a voxel outside and adjacent to a current boundary that is based on at least one of the center voxel and the center distance or a watershed boundary belongs to a background set or a first part-solid set;
    determine whether the voxel belongs to a solid tissue set or a second part-solid set based on a Markov model and on an amplitude range for solid tissue voxels and the amplitude range for part-solid voxels;
    determining a refined boundary by moving the current boundary to encompass the voxel if the voxel belongs to the first part-solid set and to the second part-solid set; and
    presenting on a display device output image data based at least in part on the location and size of the target object or the refined boundary,
  wherein the amplitude range for part-solid voxels overlaps on one end the amplitude range for solid tissue voxels and overlaps on the opposite end the amplitude range for background voxels.

18. A non-transitory computer-readable medium carrying one or more sequences of instructions, wherein execution of the one or more sequences of instructions by one or more processors causes the one or more processors to perform the steps of:
  obtain image data that indicates amplitude values at each of a plurality of voxels for a particular measurement modality;
  determine an outer edge of a contiguous subset of voxels based on voxels that have an amplitude in a first amplitude range associated with a target object in image data of the particular measurement modality;
  determine for the target object a single center voxel inside the outer edge, wherein a center distance from the center voxel to a closest voxel of the outer edge is greater than a distance from any neighbor of the center voxel to a corresponding closest voxel of the outer edge;
  determine a location and size of the target object in the image data based on the center voxel and the center distance further comprising:
    generate a plurality of rays originating at the center voxel in a corresponding plurality of directions in three dimensions;
    convert the plurality of rays in three dimensions to a plurality of adjacent rays in two dimensions;
    generate a series of amplitudes at a corresponding plurality of distances from the center voxel along each ray of the plurality of rays, each amplitude along a ray of the plurality of rays based on an amplitude of a nearest voxel to each distance from the center voxel of the corresponding plurality of distances from the center voxel; and
    generate an initial boundary based on connecting a path of minimum cost from one position on each ray of the plurality of rays to one position on each of a plurality of adjacent rays; and
  present on a display device output image data based at least in part on the initial boundary.

19. A system comprising:
  a display device;
  at least one processor; and
  at least one memory including one or more sequences of instructions, the at least one memory and the one or more sequences of instructions configured to, with the at least one processor, cause an apparatus to perform at least the following:
    obtain image data that indicates amplitude values at each of a plurality of voxels for a particular measurement modality;
    determine an outer edge of a contiguous subset of voxels based on voxels that have an amplitude in a first amplitude range associated with a target object in image data of the particular measurement modality;
    determine for the target object a single center voxel inside the outer edge, wherein a center distance from the center voxel to a closest voxel of the outer edge is greater than a distance from any neighbor of the center voxel to a corresponding closest voxel of the outer edge;
    determine a location and size of the target object in the image data based on the center voxel and the center distance further comprising:
      generate a plurality of rays originating at the center voxel in a corresponding plurality of directions in three dimensions;
      convert the plurality of rays in three dimensions to a plurality of adjacent rays in two dimensions;
      generate a series of amplitudes at a corresponding plurality of distances from the center voxel along each ray of the plurality of rays, each amplitude along a ray of the plurality of rays based on an amplitude of a nearest voxel to each distance from the center voxel of the corresponding plurality of distances from the center voxel; and
      generate an initial boundary based on connecting a path of minimum cost from one position on each ray of the plurality of rays to one position on each of a plurality of adjacent rays; and
    present on a display device output image data based at least in part on the initial boundary.

* * * * *